(12) United States Patent
Gelissen et al.

(10) Patent No.: US 10,729,324 B2
(45) Date of Patent: Aug. 4, 2020

(54) CALCULATING A HEALTH PARAMETER

(71) Applicant: KONINKLIJKE PHILIPS N.V., Eindhoven (NL)

(72) Inventors: Jozef Hubertus Gelissen, Herten (NL); John Cronin, Bonita Springs, FL (US); Lili-Marjan Brockhuis, Roermond (NL); Christopher Michael Huffines, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 184 days.

(21) Appl. No.: 15/532,653

(22) PCT Filed: Dec. 1, 2015

(86) PCT No.: PCT/IB2015/059235
§ 371 (c)(1),
(2) Date: Jun. 2, 2017

(87) PCT Pub. No.: WO2016/088027
PCT Pub. Date: Sep. 6, 2016

(65) Prior Publication Data
US 2017/0360299 A1    Dec. 21, 2017

Related U.S. Application Data

(60) Provisional application No. 62/087,741, filed on Dec. 4, 2014, provisional application No. 62/087,434, filed on Dec. 4, 2014.

(51) Int. Cl.
*A61B 5/00* (2006.01)
*G01S 19/19* (2010.01)
*G06F 19/00* (2018.01)

(52) U.S. Cl.
CPC ............ *A61B 5/0024* (2013.01); *A61B 5/486* (2013.01); *A61B 5/4866* (2013.01);
(Continued)

(58) Field of Classification Search
None
See application file for complete search history.

(56) References Cited

U.S. PATENT DOCUMENTS 8,762,102 B2 * 6/2014 Yuen .................... A61B 5/6838
702/160
9,081,534 B2 * 7/2015 Yuen ....................... G06F 11/00
(Continued)

FOREIGN PATENT DOCUMENTS

CN           103727956 A      4/2014
WO    WO-2014001947 A1 *   1/2014   ............. G01S 19/49

Primary Examiner — Carl H Layno
Assistant Examiner — Manolis Pahakis

(57) ABSTRACT

A wearable device may take a set of health inputs from embedded body sensors for the duration of an activity performed by a user of the wearable device. Based on these inputs, the wearable device can calculate a health parameter (e.g., calories burned during the activity). The wearable device can also track its location during the activity, and provide this location to a geolocation data network. The geolocation data network may provide geolocation data (e.g., weather/environmental/terrain data) pertaining to the wearable device's location. The wearable device can then modify its measurements and/or calculated health parameters based on the geolocation data (e.g. Increasing calories burned during a run due to high heat and uphill terrain in the location of the run).

11 Claims, 22 Drawing Sheets

(52) U.S. Cl.
CPC ............ *A61B 5/7278* (2013.01); *G01S 19/19* (2013.01); *G06F 19/3481* (2013.01); *A61B 5/6801* (2013.01)

(56) References Cited

U.S. PATENT DOCUMENTS

| | | | | |
|---|---|---|---|---|
| 9,619,626 | B2* | 4/2017 | Kang | A61B 5/1123 |
| 9,658,066 | B2* | 5/2017 | Yuen | G06K 9/22 |
| 9,669,262 | B2* | 6/2017 | Yuen | H04W 4/023 |
| 9,730,025 | B2* | 8/2017 | Yuen | H04W 4/029 |
| 2004/0094613 | A1* | 5/2004 | Shiratori | A61B 5/1118 235/105 |
| 2004/0122297 | A1 | 6/2004 | Stahmann et al. | |
| 2006/0064277 | A1* | 3/2006 | Jung | A63B 24/0062 702/160 |
| 2006/0230108 | A1* | 10/2006 | Tatsuta | A61B 5/0002 709/204 |
| 2009/0048044 | A1* | 2/2009 | Oleson | A63B 24/0062 473/570 |
| 2010/0010774 | A1* | 1/2010 | Ma | G01C 22/006 702/160 |
| 2011/0276312 | A1* | 11/2011 | Shalon | A61B 5/11 702/187 |
| 2012/0291544 | A1* | 11/2012 | Kawabe | A61B 5/11 73/488 |
| 2013/0041617 | A1* | 2/2013 | Pease | A61B 5/1118 702/139 |
| 2013/0090881 | A1 | 4/2013 | Janardhanan et al. | |
| 2013/0138394 | A1* | 5/2013 | Shiga | G01C 22/006 702/160 |
| 2013/0191034 | A1 | 7/2013 | Weast et al. | |
| 2013/0197857 | A1 | 8/2013 | Lu et al. | |
| 2013/0325396 | A1* | 12/2013 | Yuen | G01C 22/006 702/160 |
| 2014/0039840 | A1* | 2/2014 | Yuen | A61B 5/6838 702/189 |
| 2014/0114677 | A1 | 4/2014 | Holmes | |
| 2014/0128778 | A1* | 5/2014 | Chan | A61B 5/1116 600/595 |
| 2014/0195018 | A1* | 7/2014 | Kang | A61B 5/1123 700/91 |
| 2014/0316305 | A1* | 10/2014 | Venkatraman | A61B 5/1112 600/595 |
| 2015/0066422 | A1* | 3/2015 | Zhang | A61B 5/1126 702/141 |
| 2015/0173037 | A1* | 6/2015 | Pijl | A61B 5/1117 455/456.1 |
| 2016/0089033 | A1* | 3/2016 | Saponas | A61B 5/0205 600/483 |

* cited by examiner

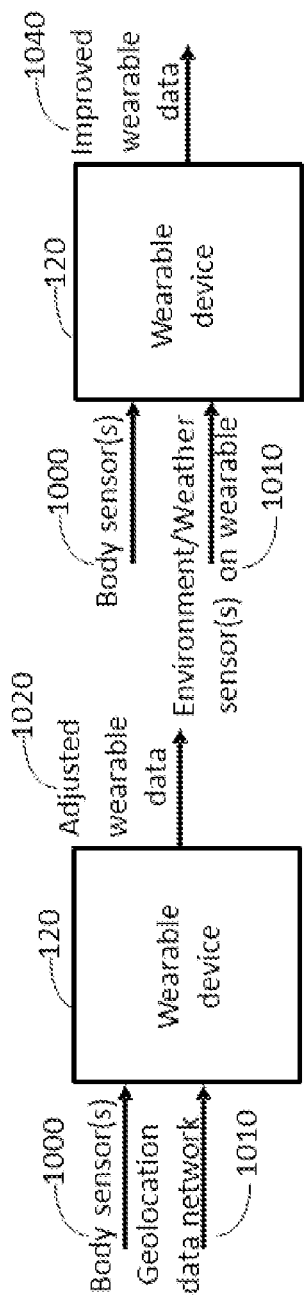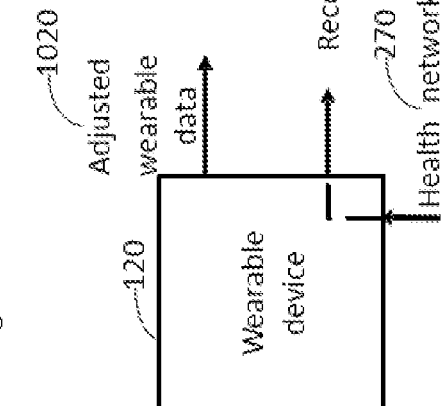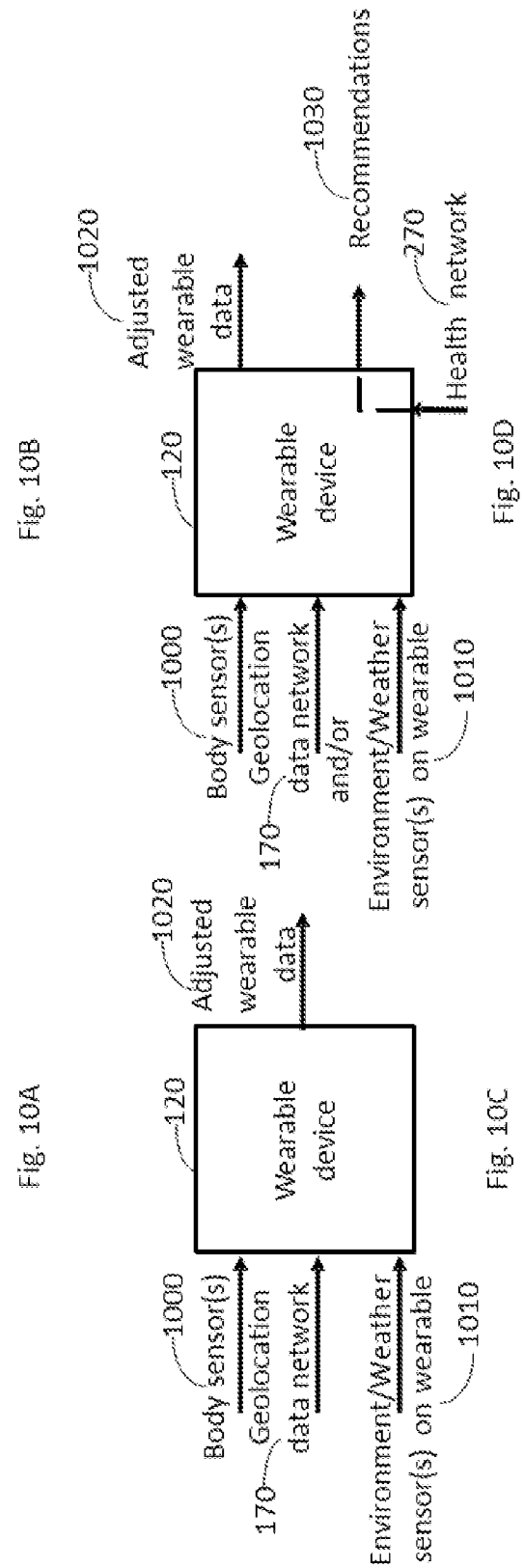

|  | Calculated Parameter Without Conversion | Calculated Parameter With Conversion | Difference | Ratio |
|---|---|---|---|---|
| L1 | 300 | 482 | 183 | 1.607 |
| L2 | 243 | 432 | 189 | 1.778 |

FIG. 11B

| History database 140, 256 | | Weather sensor temp (°F) 1615 | Weather network temp (°F) | Adjusted Blood Pressure 1620 1625 | Health Summary 1630 |
|---|---|---|---|---|---|
| Date 1610 | Body sensor Blood Pressure | | | | |
| 6-1-10 | 95 | 71 | 72 | 95 | BP OK |
| 6-2-10 | 95 | 73 | 73 | 95 | BP OK |
| 7-3-10 | 96 | 70 | 70 | 96 | BP OK |
| 12-2-10 | 101 | 19 | 20 | 96 | BP OK |
| 6-1-10 | 95 | 72 | N/A | 95 | BP OK |
| 6-2-10 | 95 | 73 | N/A | 95 | BP OK |
| 12-2-11 | 111 | 19 | 20 | 101 | BP HIGH |

Rule database

Example adjustment:

15° increase in 50°F = 1° per 10° calibration

Off average

FIG. 16

CALCULATING A HEALTH PARAMETER

CROSS-REFERENCE TO RELATED APPLICATIONS

This application is the U.S. National Phase application under 35 U.S.C. § 371 of International Application No. PCT/IB2015/059235, filed on Dec. 1, 2015, which claims the benefit of both Provisional Application Ser. No. 62/087,741, filed Dec. 4, 2014 and Provisional Application Ser. No. 62/087,434, filed Dec. 4, 2014. These applications are hereby incorporated by reference herein.

BACKGROUND

Technical Field

The present invention generally relates to wearable technology, and more specifically to the use of location and environmental inputs to calculate health parameters.

Description of the Related Art

Wearable technology is a new class of electronic systems that can provide data acquisition through a variety of unobtrusive sensors that may be worn by a user. The sensors gather information, for example, about the environment, the user's activity, or the user's health status. However, there are significant challenges related to the coordination, computation, communication, privacy, security, and presentation of the collected data. Additionally, there are challenges related to power management given the current state of battery technology. Furthermore, analysis of the data is needed to make the data gathered by the sensors useful and relevant to end-users. In some cases, additional sources of information may be used to supplement the data gathered by the sensors. The many challenges that wearable technology presents require new designs in hardware and software.

Typical wearable devices calculate various health parameters, such as calorie expenditure, hydration, and distance traveled. Further, these devices also in various occasions calculate health parameters based on the activity performed, e.g., walking, cycling, and swimming. Though these devices have many of these possibilities for the user, there is still room for improvement.

SUMMARY

A first aspect of the present invention includes a method for health calculations. Such methods may include receiving a health input from a wearable device worn by a user where such health input includes one or more measurements from one or more health sensors, calculating a health parameter based on the health input, obtaining location-based information associated with the wearable device, and modifying the calculated health parameter based on the location-based information.

Revising a calculated health parameter utilizing location-based information offers several advantages, including but not limited to, the calculation of a more accurate health parameter, the elimination of environmental-induced inaccuracies from the calculation, and improved decisions utilizing the revised parameters. For instance, if the person is running uphill, which essentially means that he has to put more effort to complete the run, overall energy expenditure must be accordingly adjusted.

In further embodiment, the method includes transmitting a location of the wearable device to a network server.

In further embodiment, the method includes receiving location-based information associated with a location of the wearable device from the network server.

In further embodiment, the method includes storing the modified health parameter in a memory of the wearable device.

In further embodiment, the method includes classifying the health input into an activity based on the location-based information and modifying the calculated health parameter based on the classification of the health input. This is in particular advantageous as calculation of health parameters depend on the type of detected activity. For instance, cycling, running, walking, each has a different calculation of calorie expenditure. In the current embodiment of the present invention, it offers several advantages concerning health calculations, including the interpretation of movement data to more accurately categorize activities and utilize that categorization to more accurately determine health related parameters of a user. These embodiments may utilize physiological, environmental, and geolocational data to improve categorizations and eliminate false positives.

In further embodiment, the location-based information may include environmental information. The environmental information may include at least one of location, outdoor humidity, outdoor temperature, outdoor ultraviolet radiation, outdoor pollen density, outdoor wind direction, outdoor wind velocity, outdoor terrain roughness, outdoor road condition, outdoor trail condition, current season, indoor temperature, indoor humidity, gym equipment resistance, gym equipment difficulty level, and environmental stress level.

In further embodiment, the method includes receiving an environmental input from the wearable device and modifying the calculated health parameter based on the environmental input. The environmental input may include one or more measurements from one or more environmental sensors concerning an ambient environmental value.

In further embodiment, the method includes generating an alert to notify the user of the wearable device about a recommendation. The alert may be at least one of displaying a text notification, displaying a graphical notification, displaying a video notification, playing an audio notification, and initiating a vibration notification. In a further embodiment of the invention, the recommendation is based on the modified health parameter. For instance, if the person is running uphill in a sunny day, then the recommendation can be based on the calculated health parameter.

In further embodiment, the method includes generating an alert based on the modified health parameter.

In further embodiment, the location-based information corresponding to the location of the wearable device is an average of a plurality of location-based data points stored at the network server corresponding to a predetermined radius of the location of the wearable device.

In further embodiment, the method includes transmitting an algorithm used to modify the calculated health parameter based on the location-based information from the network server memory to a second wearable device.

In further embodiment, modifying the calculated health parameter includes modifying the calculated health parameter using rules that are specific to the type of health parameter.

In further embodiment, the one or more health sensors may measure at least one of a blood oxygen level, a hydration level, a blood pressure, a blood sugar level, a blood glucose level, an insulin level, a body temperature, a heart rate, a weight, a sleep quality, a number of steps, a velocity of movement, an acceleration of movement, a vitamin level, a respiratory rate, a heart sound, a breathing sound, a skin moisture, a sweat level, a sweat composition, and a nerve firing.

A second aspect of the present invention includes a system for personalized health calculations with location-improved accuracy. Such systems may include a wearable device and a network server. The wearable device may include one or more health sensors that provides one or more measurements regarding a health input, a communication interface that communicates over a wireless communication network to transmit a location of the wearable device to the network server and to receive location-based information from the network server where the location-based information corresponding to the location of the wearable device, a processor that executes instructions to modify the health input based on the location-based information, and memory that stores the modified health input.

According to a third aspect of the invention, a computer program product including the computer implemented method as described above is provided. There are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the disclosure are defined in the dependent claims. It should be understood that the claimed system and the claimed non-transitory computer readable storage medium can have similar preferred embodiments and the corresponding advantages as the claimed method and as defined in the dependent method claims.

The foregoing and other features and advantages of the present invention will be made more apparent from the descriptions, drawings, and claims that follow. One of ordinary skill in the art, based on this disclosure, would understand that other aspects and advantages of the present invention exist.

BRIEF DESCRIPTION OF THE DRAWINGS

FIG. 10A illustrates an exemplary wearable device that includes input from body sensor(s), input from environment/weather sensor(s), and an output comprising improved weather data.

FIG. 10B illustrates an exemplary wearable device that includes input from body sensor(s), an input over which communications from a geolocation data network are received, and that outputs an adjusted health parameter.

FIG. 10C illustrates an exemplary wearable device that includes input from body sensor(s), input from geolocation data network, input from environment/weather sensor(s), and that outputs an adjusted health parameter.

FIG. 10D illustrates an exemplary wearable device that includes all of the elements of FIG. 10C, but further includes a communication interface receiving information from a health network and outputting recommendations.

FIG. 11B illustrates an exemplary conversion database.

FIG. 16 illustrates an exemplary history database of the wearable device and/or an exemplary history database of user device.

DETAILED DESCRIPTION

Figure 1:
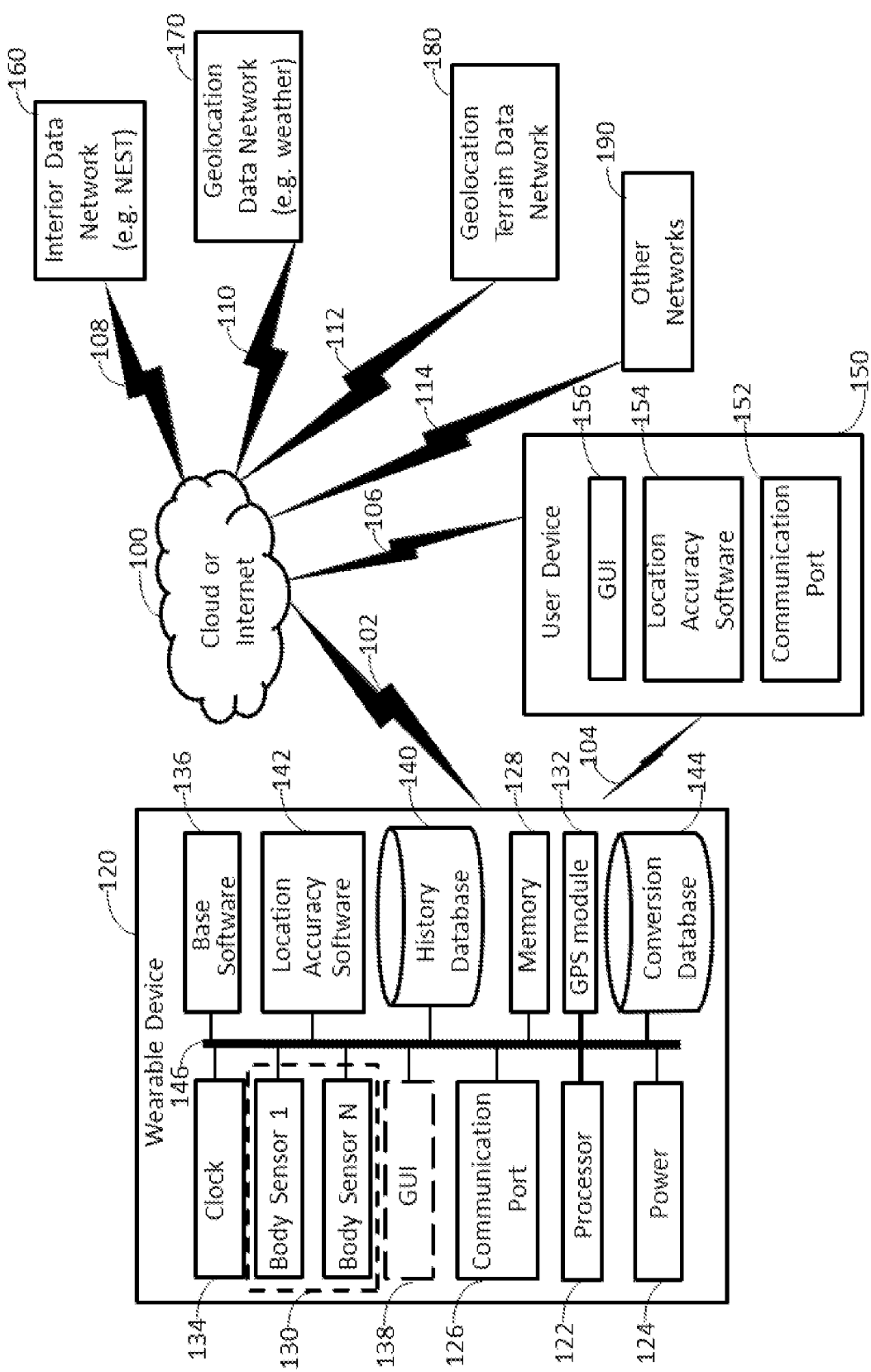
FIG. 1 illustrates a computer networked environment where a wearable device, an optional user device, and several geolocation data networks may communicate over a network.

FIG. 1 illustrates a system in accord with the present invention where a wearable device 120, an optional user device 150, and several data networks (160, 170, 180, and 190) may communicate over a network 100.

Examples of currently available wearable devices include the Apple Watch, FitBit, Jawbone Up, and the Garmin Forerunner. Within the exemplary wearable device 120, a number of elements are included which are all connected to a central bus 146. The elements include: a clock 134, one or more body sensors (1-N) 130, an optional graphical user interface (GUI) 138, a wired and/or wireless communication port 126 (e.g., a USB port module, a FireWire port module, a Lightning port module, a Thunderbolt port module, a Wi-Fi connection module, a 3G/4G/LTE cellular connection module, a Bluetooth connection module, a Bluetooth low energy connection module, a Bluetooth Smart connection module, a near field communication module, and a radio wave communications module), a processor 122, a power supply 124 (e.g., a rechargeable or non-rechargeable battery), a base software 136, a location accuracy software 142, a history database 140, a memory 128, a conversion database 144, and a global positioning system (GPS) module 132.

The clock 134 can be a system clock which is used to record both time and also time elapsed (e.g., stopwatch). A communication device (e.g., communication port 126) may be used together with or in place of the clock 134 to obtain accurate time from an outside source (e.g., cellular phone tower, NTP server, etc.).

The one or more body sensors 130 can be used to provide any number of health inputs associated with the user (e.g., blood oxygen level, hydration, blood pressure, blood sugar, blood glucose, insulin, body temperature (e.g., thermometer), heart rate, weight, sleep, number of steps (e.g., pedometer), velocity or acceleration (e.g., accelerometer), vitamin levels, respiratory rate, heart sound (e.g., microphone), breathing sound (e.g., microphone), movement speed, skin moisture, sweat detection, sweat composition, nerve firings (e.g., electromagnetic sensor), or similar health measurements). The body sensors 130 could also be used for other measurements (e.g., steps taken) which in turn could be used to calculate related health parameters (e.g., distance traveled, calories burned).

Figure 2:
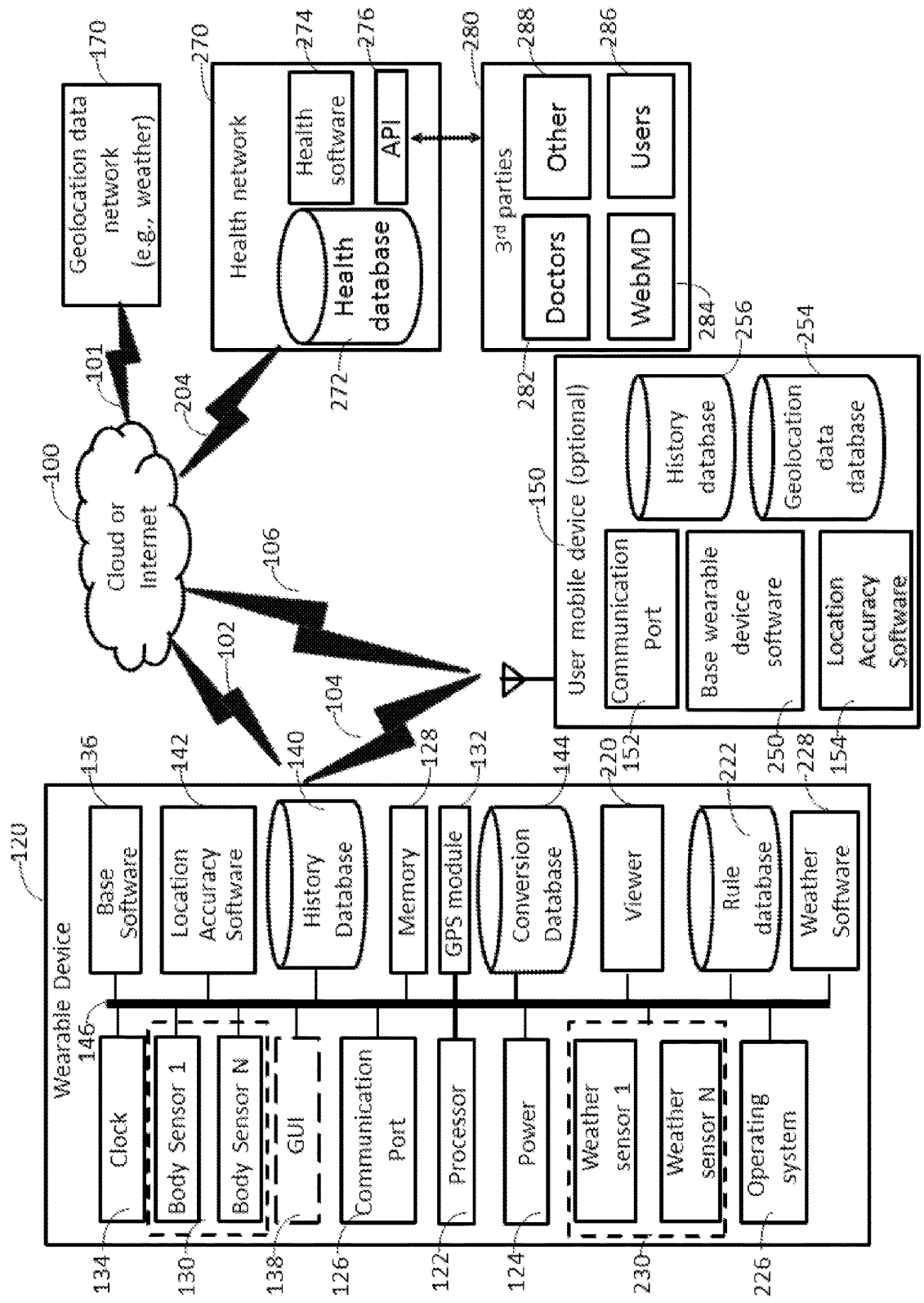
FIG. 2 illustrates a computer networked environment where a wearable device, an optional user device, a geolocation data network, and a health network may communicate over a network.

The GUI 138 can facilitate the user in creating settings and viewing data (e.g., amount of calories burned) on a display of the wearable device 120 (e.g., viewer 220 illustrated in FIG. 2). In embodiments where a GUI 138 is not included in the wearable device 120, another interface can be provided in a tethered user device 150 where the user device 150 is designed to provide further computing and/or interface functionalities to the wearable device 120.

The communication module 126 may be used by the wearable device 120 to communicate with other devices and networks over a network. The communication module may be wireless, cellular, near field communication (NFC), Bluetooth, etc.

The base software 136, which can be seen in FIG. 1, is the software that is used to calculate various health parameters (e.g., calories burned or distance traveled) based on the sensor data obtained from the one or more body sensors 130. However, these health parameters initially calculated by the base software 136 are not yet modified by any external data (e.g., from data networks 160, 170, 180, and 190 from FIG. 1 and from data network 270 from FIG. 2) corresponding to the location of the user.

The location accuracy software 142, as provided for the wearable device 120 in FIG. 1, takes external data (e.g., from data networks 160, 170, 180, and 190 from FIG. 1 or from data network 270 from FIG. 2) based on the user's current location (e.g., the location of the wearable device 120) and modifies the output from the base software 136 to derive a more accurate health parameter.

The history database 140 is a storage for sensor data. The location accuracy software 142 may retrieve sensor data from the history database 140 to produce a modified or "converted" health parameter that takes into account geolocation data (e.g., weather data).

Figure 8:
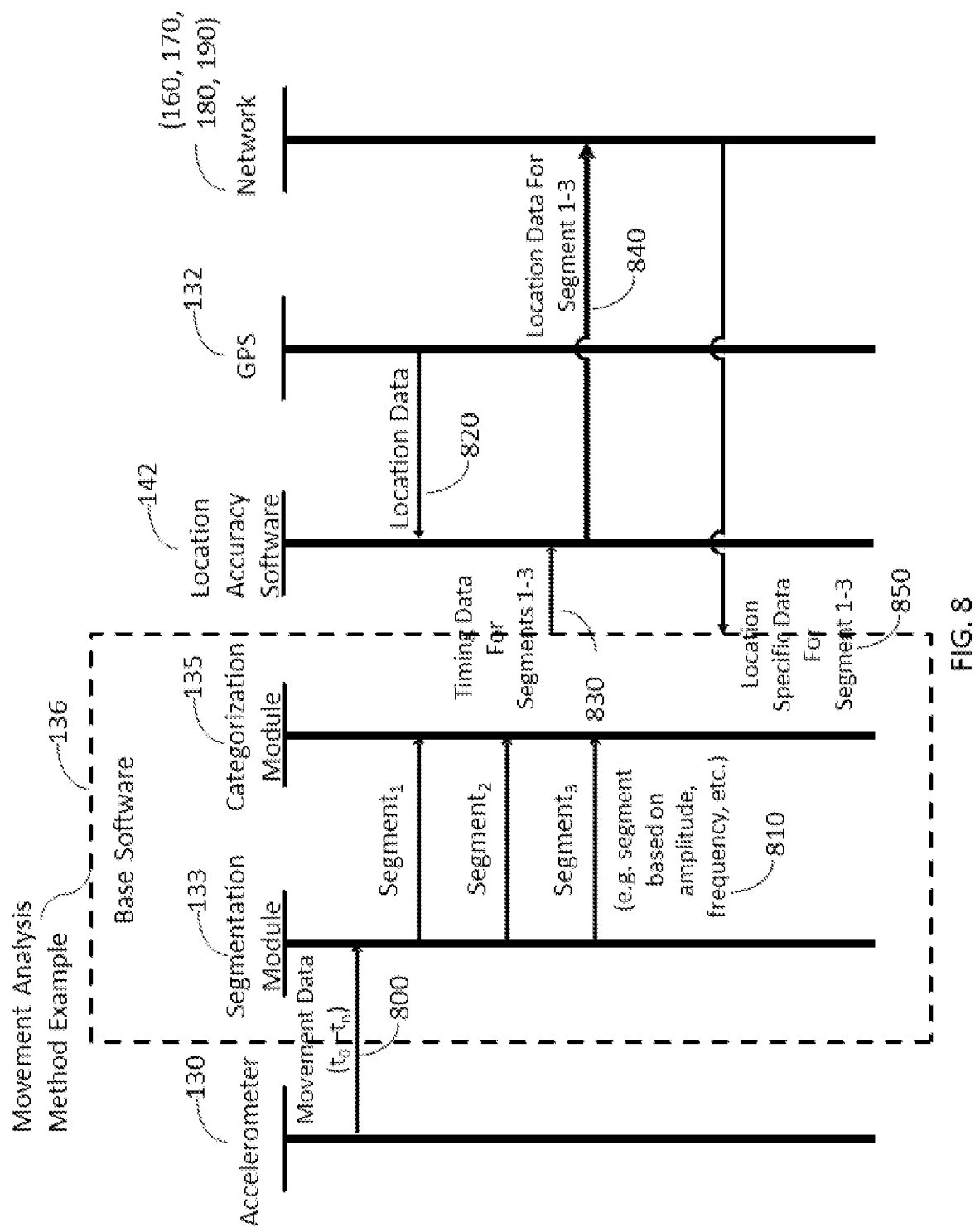
FIG. 8 illustrates an exemplary lane diagram showing the method for classifying movement data illustrated in FIG. 7, and executed by the systems in FIG. 1 and FIG. 2 and the base software illustrated in FIG. 6.

The conversion database 144 may contain pre-determined algorithmic conversion data that can be used to calculate the modified or "converted" health parameter that takes into account both data from body sensors 130 and geolocation data (e.g., weather, terrain) (see e.g., step 800 of FIG. 8).

The GPS module 132 is used to determine a user's exact geolocation (e.g., the location of the wearable device) for the wearable device 120 to use and/or to provide to sources of external data (e.g., from data networks 160, 170, 180, 190 from FIG. 1 or and from data network 270 from FIG. 2).

It should be noted that the wearable device 120 can, in some embodiments, communicate over a network 100 (e.g., connection 102) as well as directly with a user device 150 (e.g., connection 104) (e.g., via a wire, a Bluetooth connection, or a Wi-Fi direct connection). The user device 150 can be a smart phone, a tablet, a desktop computer, a laptop computer, a gaming console, a smart television, a home entertainment system, a second wearable device, or any other device the user may use to interact with the wearable device 120. The user device 150 itself includes a communication port 152 (e.g., a USB port module, a FireWire port module, a Lightning port module, a Thunderbolt port module, a Wi-Fi connection module, a 3G/4G/LTE cellular connection module, a Bluetooth connection module, a Bluetooth low energy connection module, a Bluetooth Smart connection module, a near field communication module, a radio wave communications module, etc.).

The user device 150 can also include a GUI 156, especially in situations where the wearable device 120 does not have its own GUI 138. The user device 150 also executes a location accuracy software 154. The software facilitates the user device 150 to run corresponding location accuracy algorithms on the user device 150 instead of on the wearable device 120 and can be seen as being similar to the location accuracy software 142 included in the wearable device 120.

Similarly to the wearable device 120, the user device 150 may also be connected to the network 100 (e.g., connection 106), and through this connection, is connected to the plurality of data networks (e.g., data networks 160, 170, 180, and 190 from FIG. 1 or data network 270 from FIG. 2) (e.g., connections 108, 110, 112, or 114 of FIG. 1 and connections 202 and 204 of FIG. 2). As shown in FIG. 1, exemplary networks include the Interior Data Network 160 (e.g., related to a Nest Learning Thermostat or Apple Homekit framework), Geolocation Data Network 170, Geolocation Terrain Data Network 180 and other networks 190. In particular, the networks represented can be used to provide the wearable device 120 and/or user device 150 with location-specific data which can be used to modify calculations to provide a more accurate health parameter. For example, the interior data network 160 can be used to provide environmental inputs such as the indoor temperature and humidity data for the wearable device 120 and/or user device 150. In contrast, the Geolocation Data Network 170 can provide weather conditions for a particular geolocation. With the Geolocation Terrain Data Network 180, the wearable device 120 and/or user device 150 can obtain environmental inputs such as the environmental temperature, wind speed and direction in the area where the user was located. Furthermore, information in the Geolocation Terrain Data Network 180 may include details about the actual terrain (e.g., terrain material, incline, type of soil, type of bedrock). Lastly, the other networks available in the system may include any other location-specific data that may be useful in modifying health parameter using the location accuracy algorithms (e.g., locations about parks, trails, humidity). Other networks 190 (e.g., healthcare providers) may provide other location-specific data that might impact a user's sensor measurements (e.g., blood pressure measured) or health parameter calculations (e.g., calories burned). For example, one other network 190 might provide location-based stress level data. For example, a user located at the subway system of a packed urban environment would be in a higher-stress-level environment than a user located in a peaceful countryside by a calm lake. A user in a higher-stress-level environment might be burning more calories simply by virtue of being in a crowded or potentially dangerous area (e.g., the user might need to periodically check if a car or train is coming so that he/she is not hit).

Because data networks (e.g., data networks 160, 170, 180, and 190) might not contain location-specific data for every possible location that a wearable device 120 might go, in such situations, a data network (e.g., data networks 160, 170, 180, and 190) may provide the data corresponding to the nearest geolocation, or an average of the nearest geolocations within a predetermined radius around the requesting location.

As an example embodiment, this system can be used to provide a more accurate calculation of the amount of calories burned during a run. Generally, the user wears or has on his body the wearable device 120. The one or more body sensors 130 obtain health input data about the user (e.g. pulse, breathing rate). Each sensor measurement of the health input data has an associated clock time stamp. The base software 136 calculates an initial amount of calories burned for that run using the health input data, the time stamp, the distance run, etc. Using the GPS module 132, the wearable device 120 can identify where the user is during the run. By using the communication system, the wearable device can access one or more networks (e.g., data networks 160, 170, 180, and 190 from FIG. 1 and data network 270 from FIG. 2) to retrieve location-specific data relating to the location of the run. The location-specific data is used in the location accuracy software 142 to provide more accurate calculations of the calories burned (e.g., by factoring in data about the temperature/weather that the user was running in, the elevations and inclines the user ran over, etc., each of which may have an effect on the number of calories burned).

In some embodiments, the wearable device 120 may itself contain location-specific data which may be used to adjust the calculated health parameter as disclosed herein. For example, the wearable device 120 may contain downloaded maps, terrain information, weather forecasts, etc.

FIG. 2 illustrates another system in accord with the present invention where a wearable device 120, an optional user device 270, a geolocation data network 170, and a health network 270 may communicate over a network 100. The network environment includes communication pathways 102, 104, 106, 101, and 204, where communication pathways 102, 106, 101, and 204 go through a network 100. Communication pathway 104 is a direct communication path that may be used when the wearable device 120 communicates directly with the optional user device 270. Each of these communication pathways may be a wireless or a wired communication path known in the art including, but not limited to Bluetooth, Wi-Fi, Wi-Fi Direct, cellular, Ethernet, etc.

The embodiment of the wearable device 120 that is pictured in FIG. 2 may include the components and software elements of the wearable device 120 embodiment of FIG. 1, and may also include other components and software elements. For example, the exemplary wearable device 120 as illustrated in FIG. 2 may include one or more weather sensors (1-N) 230 providing one or more environmental inputs in addition to the one or more body sensors (1-N) 130. It may also include an operating system (OS) software 226, a viewer 220, a weather software 228, and a rule database 222.

The optional user device 150 may include the components and software elements of the user device 150 embodiment of FIG. 1, and may also include a base wearable device software 250, a location accuracy software 154, preferably an application (app), a history database 256, and a geolocation data database 254.

The health network 270 server may include a health database 272, a health software 274, and an application program interface (API) 276. The API 276 in the health network 270 may communicate with a set of third parties 280. Third parties may be doctors 282, online medical/health references like WebMD 284, users 286, and other third parties 288 such as caregivers or advertisers.

Regarding the data networks of FIG. 1 and FIG. 2, the interior data network 160, the geolocation data network 170, and the geolocation terrain data network 180 are focused on providing environmental inputs about a location given by the GPS module 132 of the wearable device 120. The health network 270, on the other hand, may be used to provide data, but may also back up health input data in the health database 272 (e.g., synchronizing the health database 272 with a history database 140 of a wearable device 120 or a history database 256 of a user device 150). The health network 270 may also include health software 274 that provides recommendations to the wearable device 120 based on their health measurements and/or geolocation/environment data (e.g., "be careful—your blood pressure is high," "slow down and rest—it's very hot and you seem to be dehydrated," "just a little farther—you've almost met your calorie goal!"). In some embodiments, recommendation functionality can also be offered by the interior data network 160 (e.g., recommendations to stop exercising due to high indoor temperatures or carbon monoxide presence), the geolocation data network 170 (e.g., recommendations to rest due to hot temperatures), and geolocation terrain data network 180 (e.g., recommendations to be careful due to presence of cliffs or slippery soil).

A GPS location from GPS module 132 may be used to identify the location of a user of a wearable device 120 (e.g., the location of the wearable device), where the location may be used by the health network 270 when preparing health recommendations to transmit to the wearable device 120. The optional user device 150 may be used as a proxy for the wearable device 120. When this occurs, the user device 150 may receive information from the wearable device 120, and the user device 150 may communicate over a network 100 with the health network 270, with the interior data network 160, with the geolocation data network 170, with the geolocation terrain data network 180, or with other networks 190. The user device 150 may also display recommendations received from the health network 270 or calculations from the networks of FIG. 1 on a display (e.g., through GUI 156 of FIG. 1), as well as communicate weather and/or geolocation data received to the wearable device 120.

One advantage of a user device 150 acting as a proxy for the wearable device 120 is that communications may be generally faster and/or more efficient, since a user device 150 may often have greater processing and communication capabilities than a typical wearable device 120. For example, wearable device 120 may not be capable of communicating over a cellular network (e.g., the wearable devices 120 may be limited to wired and/or Bluetooth communications), while a user device 150 can typically communicate over both a cellular network (e.g., an Edge, 3G, 4G, or "LTE" Long-Term-Evolution network) and Wi-Fi/Bluetooth networks. Another advantage of the user device 150 acting as a proxy for the wearable device 120 may be an improvement to the overall battery life of the wearable device 120.

In some embodiments, the wearable device 120 may itself contain location-specific data which may be used to adjust the calculated health parameter as disclosed herein. For example, the wearable device 120 may contain downloaded maps, terrain information, weather forecasts, etc.

Figure 3:
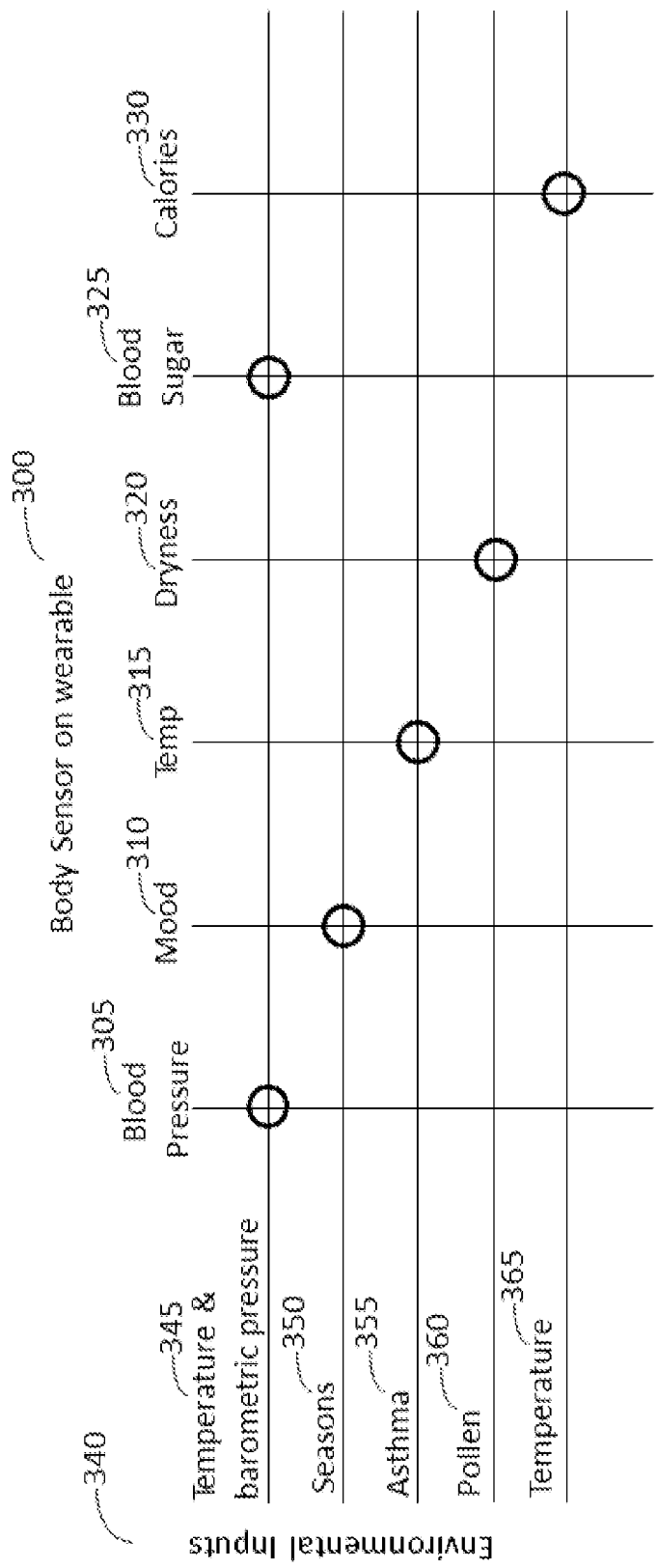
FIG. 3 illustrates an exemplary table that cross-references health input data sensed by body sensors at a wearable device with weather/geolocation data received from a weather or geolocation data network.

FIG. 3 illustrates an exemplary table that cross-references health data sensed by body sensors 130 at a wearable device 120 with geolocation and weather data received from geolocation data network 170. The table lists several exemplary body sensor types 300, and charts these against several exemplary environmental inputs 340. The exemplary body sensors 300 on the wearable device 120 include exemplary sensors for monitoring blood pressure 305, mood 310, body temperature 315, dryness 320, blood sugar 325, and calories 330. The exemplary environmental inputs 340 include temperature and barometric pressure 345, seasons 350, asthma risk levels 355, pollen density levels 360, and outdoor temperature 365.

Crosses identified in the table are identified by circles where horizontal and vertical lines intersect in the table. A first cross indicates that blood pressure 305 may be affected by temperature and barometric pressure 345. A second cross indicates that the seasons 350 may affect the mood 310 of a person, and a third cross indicates that asthma risk levels 355 may be exacerbated by a high body temperature 315. Other crosses indicate that dryness 320 and high pollen levels 360 may increase allergy symptoms, that temperature and barometric pressure 345 may affect blood sugar level 325, and that outdoor temperature 365 may affect the number of calories burned over time 330 (e.g., running in heat may cause faster calorie burn).

Crosses identified in this exemplary table may be used in some embodiments to provide recommendations to the user (e.g., "avoid running today—dangerously high pollen counts!") and can be used to modify health parameter calculations. For example, the location accuracy software 142 of the wearable device 120 (or the location accuracy software 154 of the user device 150) may increase a calculated calorie count based on the user exercising in high temperature (see, e.g., calories 330 affected by temperature 365).

Figure 4:
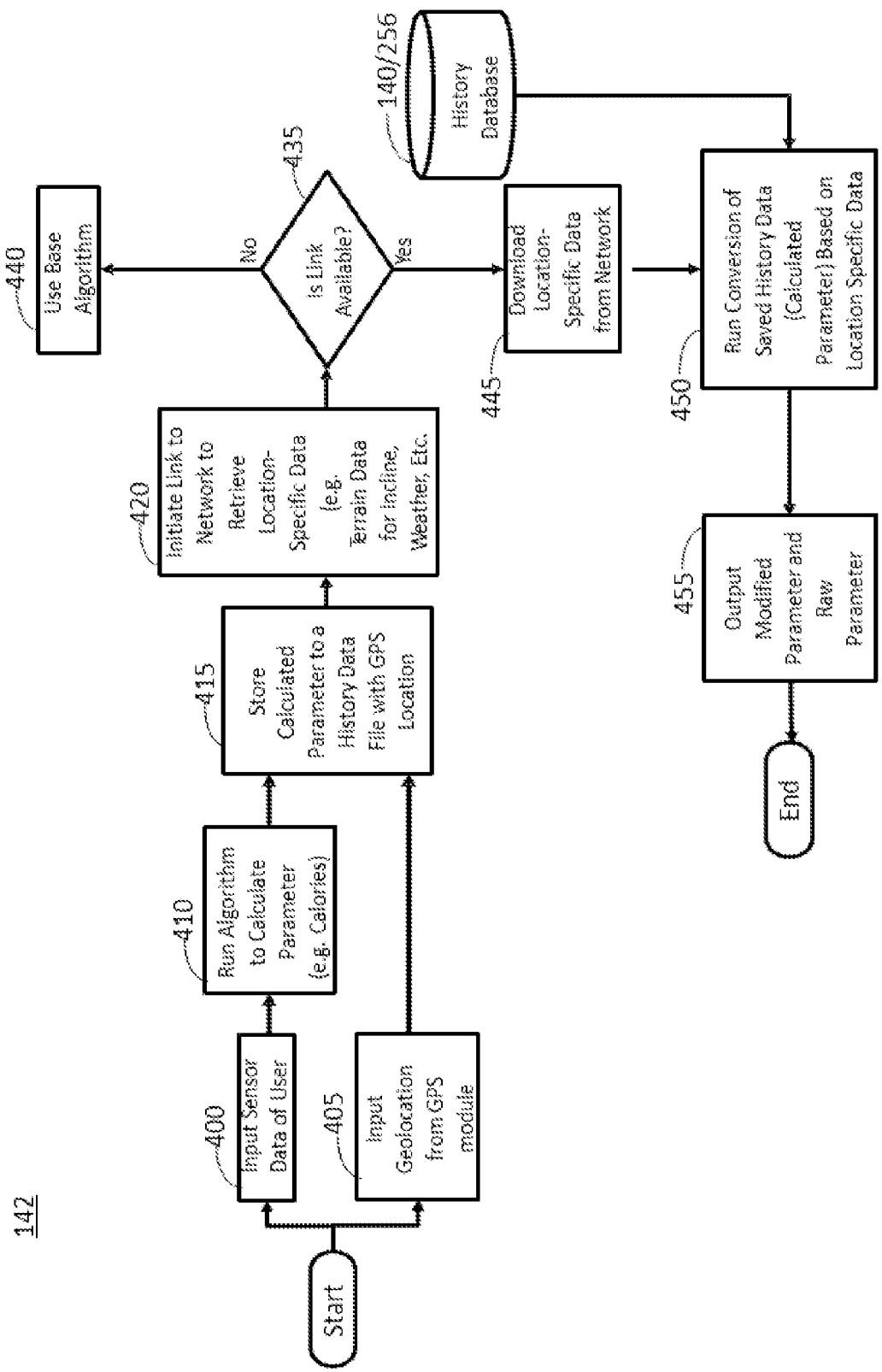
FIG. 4 illustrates an exemplary calculation operation for the base software and location accuracy software.

FIG. 4 is a flowchart for an exemplary calculation operation for the base software 136 and location accuracy software 142. The base software 136 can take in a number of inputs from the wearable device 120, which can be provided by the wearable device 120 itself or provided by the user. As seen in FIG. 2, the base software 136 takes inputs from the one or more body sensors 130 found on the wearable device 120 (step 400) and also takes inputs relating to the geolocation of the user through the GPS module 132 (step 405). The plurality of sensor data includes health input data (e.g., heart rate, blood pressure, blood-oxygen levels).

With the inputted health sensor data (see step 400), the base software 136 then calculates a value for a health parameter (e.g., distance run, calories burned) (step 410). These health parameter values are stored in a history file or history database 140 and 256 with the corresponding GPS location obtained in step 405 (step 415).

The base software 136, in combination with the location accuracy software 142, then communicates with one or more of the data networks pictured in FIG. 1 and/or FIG. 2, to obtain location-specific data (e.g., interior data from interior data network 160, weather data from geolocation data network 170, health input data from health network 270, terrain data from geolocation terrain data network 180) by attempting to form a link with the one or more networks (step 420). The type of link can be a standard type of link initiated through, for example, through an application programming interface (e.g., API 276 of health network 270).

Determination if a link to a data network is available is performed (step 435). If a link to a data network is not possible at this time, the wearable device 120 displays the initial health parameter calculated by the base algorithm of the base software 136 (step 440). However, if a link to an external network is possible, then location-specific data (e.g., weather data, environmental inputs) is downloaded (step 445). Once downloaded, the location-specific data may be used by the location accuracy software 142 to modify (or "convert") the initial parameter calculation of step 410 (e.g., provide a more accurate "calories burned" value based on weather conditions) (step 450). The location accuracy software 142 may also modify (or "convert") initial calculations (see step 410) from historical sensor measurements from the body sensors 130 (e.g., stored in history database 140 of the wearable device 120 or history database 256 of the user device 150) (step 450). The location accuracy software 142 may then output the modified (or "converted") parameter value in lieu of or in addition to the "raw" parameter value calculated in step 410 (step 455). In some embodiments, the output of step 455 is displayed at the wearable device 120 (e.g., at viewer 220) or at the user device 150 (e.g., using GUI 156). In some embodiments, the output of step 455 is stored in the history database 140/256 or to a data network (e.g., to health database 272 of health network 270). In some embodiments, the output of step 455 is also stored in the history database 140 or 256. Appropriate information from the conversion database is also used in order to facilitate the modifications by the location accuracy calculations. Afterwards, the new modified health parameter is provided to the user to view.

Figure 5:
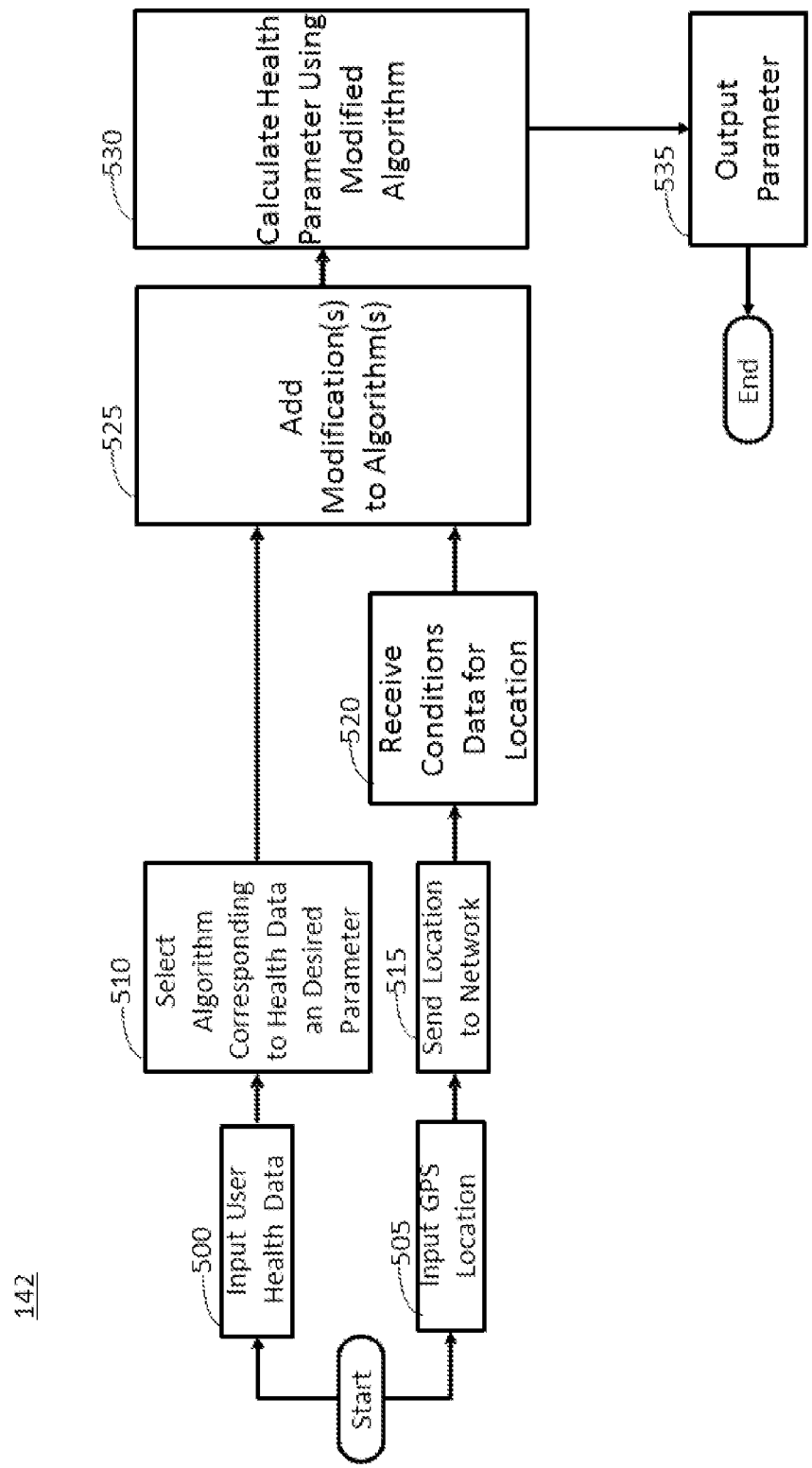
FIG. 5 illustrates another exemplary calculation operation for the base software and location accuracy software.

FIG. 5 is a flowchart for another exemplary calculation operation for the base software 136 and location accuracy software 142. As opposed to the method described in FIG. 4, the method shown in FIG. 5 uses the inputs from body sensors 130 and from the GPS module 132 in a different manner. In particular, the input sensor measurement data regarding the user's health input data is provided to the wearable device 120 (step 500) which in turn determines and selects an appropriate algorithm to use based on the health input data (step 510). The algorithm used will be dependent on the sensor measurement input received (e.g., the algorithm used to calculate a parameter such as calories burned may depend whether the sensor measures pulse, motion, or another health measurement). Meanwhile, the GPS input from GPS module 132 is also received at the wearable device 120 (step 505) and subsequently provided to one or more data networks (e.g., data networks 160, 170, 180, and 190 from FIG. 1 and data network 270 from FIG. 2) (step 515). The wearable device 120 then receives location-specific data (e.g., weather conditions, environmental conditions, terrain conditions, indoor conditions) from these one or more external networks (step 520).

At this time, both sets of data (e.g., the location-specific data from the data networks from step 520 and the output from the health parameter calculation algorithm from step 510) are combined and the health parameter algorithm is modified based on the location-specific data (step 525). By using the modified health parameter algorithm, a health parameter is then calculated (step 530) and output to the wearable device 120 (e.g. to history database 140), to user device 150 (e.g., to history database 256), or to a data network (e.g., to health database 272 of health network 270) (step 535).

In some embodiments, the health network 270 may also serve to share geolocation-based adjustments, conversion algorithms of sensor measurements, and/or health parameter calculations among wearable devices 120. That is, portions of a conversion database 144 of one wearable device 120 may be shared with other (e.g., less capable) wearable devices 120. If geolocation-based adjustment or "conversion" algorithms vary between different devices, an algorithm producing an average result between those variances could be used and given to other (e.g., less capable) wearable devices.

Similarly, other data could be "crowdsourced." For example, wearable devices could share data from their weather sensors 230 with data networks 160, 170, 180, and 190, which could then be averaged, thus producing or contributing to the data sets of data networks 160, 170, 180, and 190.

Figure 6:
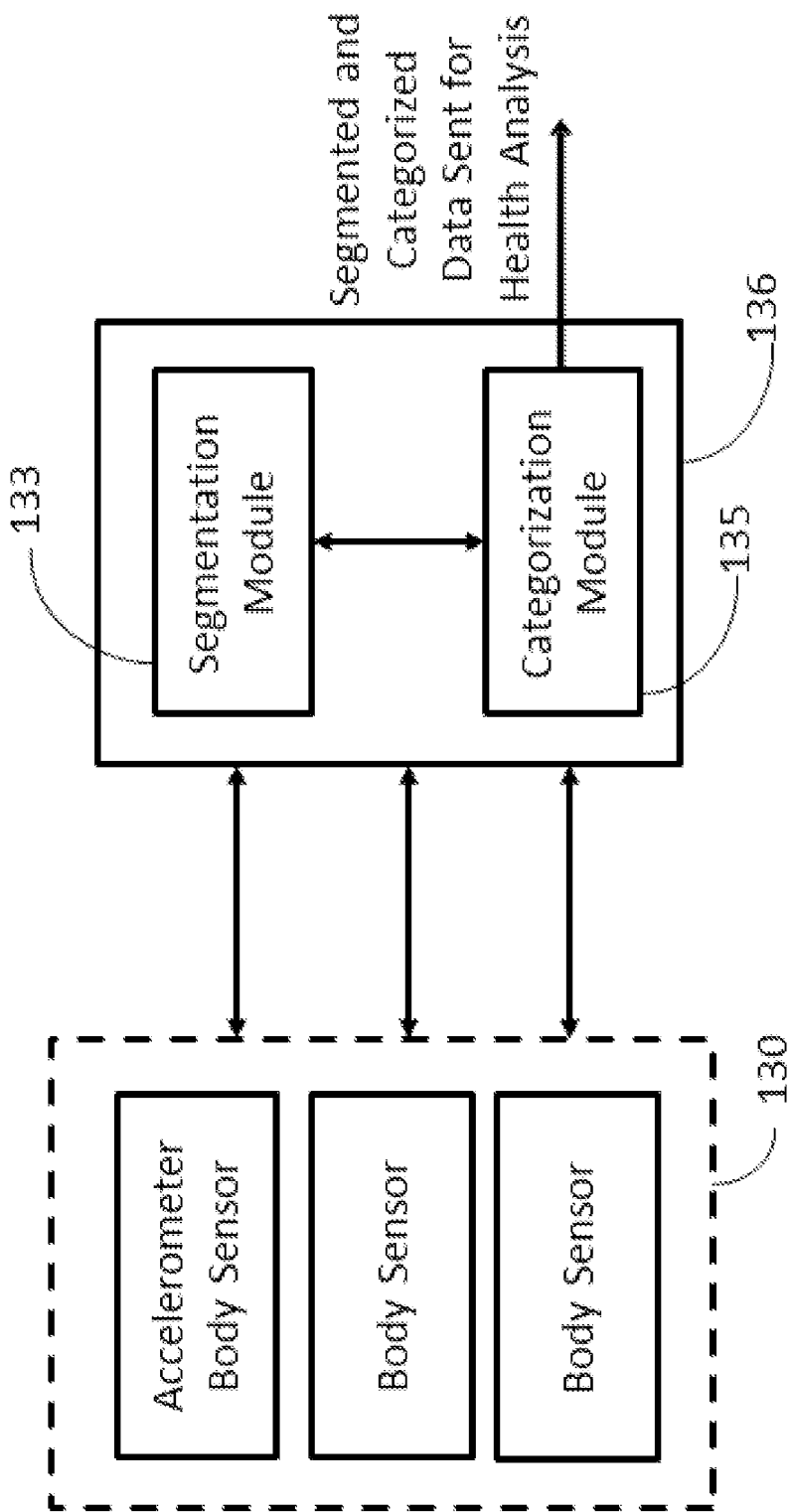
FIG. 6 illustrates a structure for base software according to an exemplary embodiment of the invention.

FIG. 6 illustrates an exemplary embodiment of a part of the system that may be utilized to analyze movement data. In various embodiments, one or more of the body sensors 130 that comprise the wearable device 120 include an accelerometer. The accelerometer may continuously capture a record of the movement (also referred to as movement data) of the wearable device 120 and thus the user wearing the wearable device 120. The movement data may be provided to the base software 136 as a health input for a calculation of health related parameters as described with reference to FIG. 4. In some cases, the movement is "active" in that the user is walking, running, swimming, etc., and the captured movement accurately reflects the user's level of activity for the determination of various health parameters related to the user's activities. In other cases, however, that movement is passive in that the user is riding in a car, on a plane, on a boat, etc., and the captured movement does not accurately reflect the user's level of activity for the determination of various health parameters related to the user's activities.

To more accurately categorize the movement data, the base software 136 includes a segmentation module 133 and a categorization module 135. The segmentation module 133 is configured to analyze and identify movement data within temporal ranges that have similar characteristics, for example, having similar amplitudes and/or frequencies. The categorization module 136 may categorize each segment as matching one or more active or passive activities such as walking, running, swimming, flying in an airplane, riding in a car, riding on a train, jogging, riding in an airplane, etc.

The categorization may be performed using a variety of techniques, including but not limited to matching segments against stored segments previously associated with a particular activity; comparing a segment against other recorded segments; comparing the parameters characterizing one or more segments against rules associating various parameters ranges with various activities; asking the user to manually identify the activity (and thereby creating a stored segment or a rule for future use), etc.

Exemplary embodiments of the base software 136 may use additional sensor data to further refine these categorizations, including but not limited to eliminating false positives or more accurately characterizing the nature of the movement detected in the captured movement data. These refinements can take a variety of forms, depending on the particular sensors available. Once categorized, the nature of the activity and its duration can be evaluated for its effect on the user's daily activity level and/or health.

One exemplary embodiment of the base software 136 utilizes location specific data to refine the categorization of the segmented movement data. For example, if the location specific data indicates that the movement occurred in a body of water and the speed of the user was approximately 5 miles per hour, then an initial categorization of walking may be refined as swimming. This characterization may be further confirmed by, for example, a temperature sensor indicating that the temperature of the mobile device is significantly cooler than that a networked-accessible source of weather data may indicate; a cardiometer indicating that the user's heart rate is higher than normal, etc.

In another example, an initial categorization of "walking" may be confirmed if the user's velocity is consistent with walking, for example, 4 mph or less. The categorization may be further refined by, for example, querying a source of terrain data for terrain information relevant to the user's positional location. A certain latitude/longitude combination may indicate that the user is in a gym, on a highway, in a river, etc. If the user is located on a highway, then the activity may be reclassified away from "walking" to "driving." If the user's personal calendar indicates that the user is taking a train, and the accelerometer data is consistent with walking, the activity may be confirmed as "walking."

This characterization may be further confirmed by, for example, a temperature sensor indicating that the temperature of the mobile device is significantly cooler than that a networked-accessible source of weather data may indicate; a cardiometer indicating that the user's heart rate is higher than normal, etc.

If the GPS unit instead indicates that the user is moving at, for example, 5+ mph in a consistent direction, while the user is in a body of water then the device may characterize the user's activity as sailing or boating. If the GPS unit instead indicates that the user is moving at, for example, 5+ mph in a varying direction, while the user is in a body of water then the device may characterize the user's activity as running (for example, on the deck of a cruise ship or around the edge of a powerboat). These characterizations could be further confirmed with the use of, for example, a temperature sensor indicating that the mobile device is at a temperature close to that of the ambient temperature indicated by a source of network-accessible weather data, a temperature sensor indicating that the ambient temperature is sub-freezing, access to the user's personal data indicating that the user is taking a cruise, etc. Swimming and running may be counted in the computation of health parameters, while sailing would not.

Similarly, if a source of network-accessible location data indicates, for example, that the user is in a gymnasium; a GPS sensor indicates that the user is stationary; but the device accelerometer indicates that the user is moving, then the mobile device may conclude that the user is utilizing a piece of exercise equipment and characterize the activity as walking or exercise depending on the characteristics of the movement measured by the accelerometer.

If a source of network indicates, for example, that the user is on a highway, the GPS unit indicates that the user is moving at 50 mph, and the accelerometer indicates the user is moving, then the mobile device may conclude that the user is driving a vehicle and may disregard the user's activity for, for example, determining whether the user has met a goal of a certain amount of physical exercise or the computation of a health parameter.

Some movements can have a similar frequency and/or speed as walking, but are more (or less) intense for the body, resulting in a higher (lower) heart rate and breathing rate, so other embodiments may utilize other health inputs (e.g., heart rate, breathing rate, and skin temperature) and environmental inputs (outdoor temperature, wind speed, etc.) in a similar fashion to characterize or assess the user's activity or improve the calculation of a health parameter (e.g. calories consumed).

Figure 7:
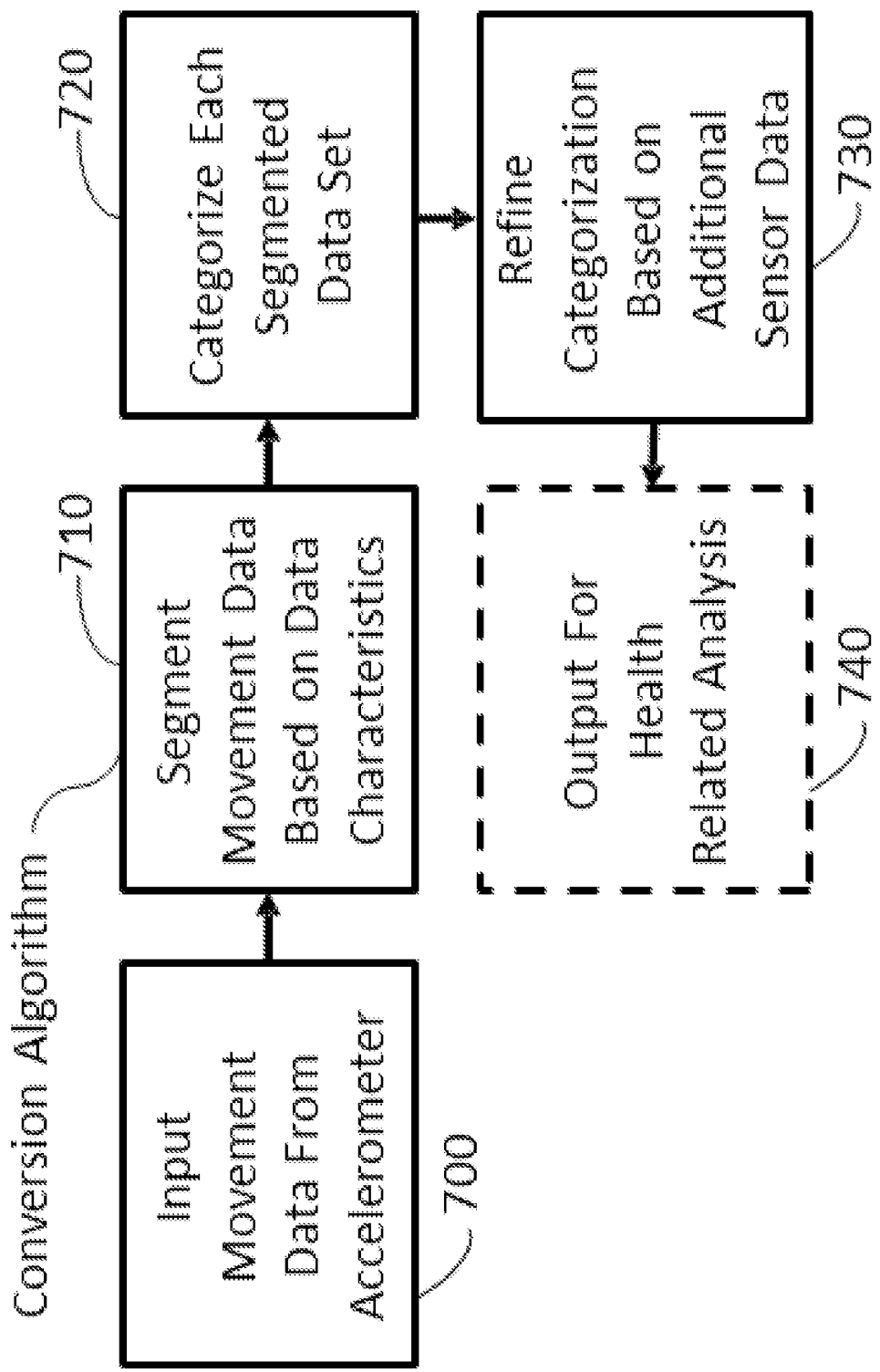
FIG. 7 illustrates an exemplary conversion algorithm for classifying movement data executed by the systems in FIG. 1 and FIG. 2 and the base software illustrated in FIG. 6.

FIG. 7 illustrates an exemplary calculation operation for the conversion algorithm executed by the base software 136 and location accuracy software 142 to segment and categorize movement data. The base software 136 receives movement data generated by the accelerometer (body sensor) 130 (Step 700). The movement data can be received directly from the accelerometer 130 or indirectly, for example, input by a user.

The segmentation module 133 segments the movement data based on data characteristics, such as amplitude and frequency of the movement data (step 710). The movement data may be segmented into discrete blocks based on timing information received by the base software 136 and associated with the movement data. Once the data is segmented, each segment is then categorized as an activity (Step 720). Next, the base software 136, in operation with additional body sensors 130, the location accuracy software 142 and the GPS 132, refines the categorization based on location specific data received from the data networks 160, 170, 180, and 190 (Step 730).

In some cases movement may reflect a hybrid scenario, for example, a user jogging around the deck of a cruise ship, a user performing isometric exercises while in a private room on a train or plane, etc. In these cases, data from a variety of sensors, including but not limited to the GPS, a terrain sensor (e.g., GPS position data used in tandem with a terrain/maps database), a thermometer, etc., may be used to determine whether the captured movement relates to a hybrid scenario and the data may be used to further refine the categorization and for the determination of various health parameters related to the user's activities.

In yet other cases, the measured movement may reflect a false positive scenario, where the user is performing an activity with, for example, an amplitude or frequency profile that matches that of another activity. For example, the user tapping his foot out of boredom may generate an accelerometer signal that resembles the accelerometer signal generated when the user is walking. Something similar may occur if a user "drums" their fingers on a surface. Another false positive may occur when a user is a passenger is a vehicle traversing bumpy terrain. Accordingly, the refinement of the categorization using the location data may be used to eliminate certain segments from being considered for the determination of various health parameters related to the user's activity.

After the movement data has been refined it is then output for health related analysis including the calculation of health parameters related to the user's activities (step 740). The wearable device 120 may display parameters and information about the activities via screen or display (digital or analog). The refined movement data and/or health related parameters may be stored in a history database (e.g., history database 140), transmitted to a public database, or transmitted to a user's account "on the cloud" that can be accessed by the user using a computer, mobile device, or other device that can connect to the user's account.

FIG. 8 is an illustration of a lane diagram showing an exemplary execution of the process described in FIG. 7 by the systems described in FIG. 1 and FIG. 6 as disclosed herein. First the movement data is received at the base software 136 from the accelerometer 130 (step 800). In this example, the data corresponds to a time range $t_0$ to $t_N$. The time range need not be continuous and could correspond to several different overlapping or non-overlapping periods. The segmentation module 133 of the base software 136 executes to segment the movement data into $Segment_1$, $Segment_2$, and $Segment_3$ according to the methods described herein (step 810). The base software 136, accuracy software 142, GPS 132 and data networks 160,170, 180, and 190 interact to acquire location specific data for $Segment_1$, $Segment_2$, and $Segment_3$. The GPS 132 sends location data to the location accuracy software 142 (step 820), that includes location data relevant to $Segment_1$, $Segment_2$, and $Segment_3$. The base software 136 sends timing information for each of the segments to the location accuracy software 142 (step 830). Based on the timing information, the location accuracy software 142 sends location data for the segments to one or more of data networks 160, 170, 180 and 190 (step 840), and the base software 136 receives location specific data for each of $Segment_1$, $Segment_2$, and $Segment_3$ (step 850). The base software 136 then may refine the categorization of the movement data based on the location specific data, and the refined movement data may be used to determine health-related parameters, such as distance traveled, calorie expenditure.

Figure 9:
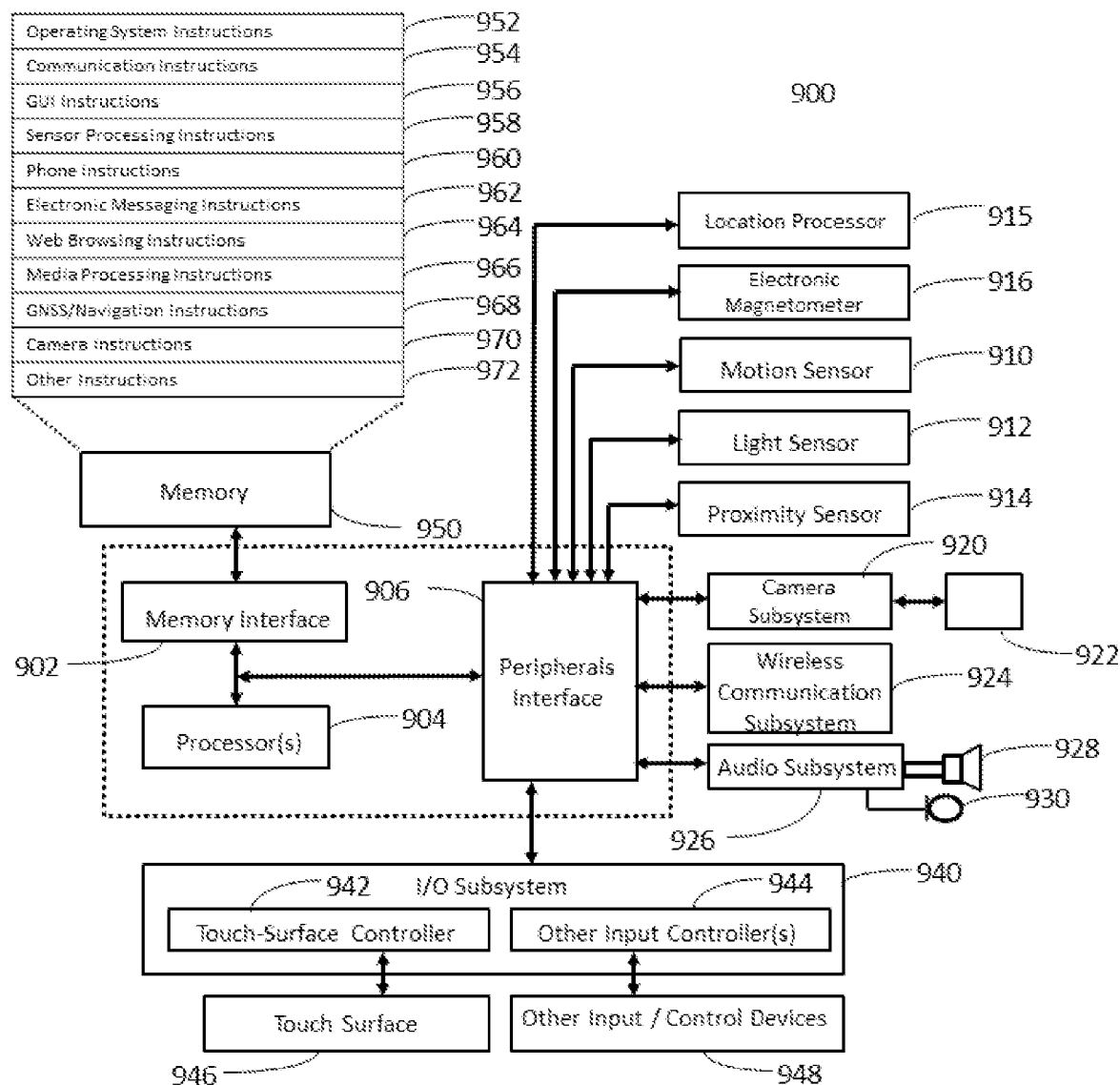
FIG. 9 illustrates an exemplary computing device architecture that may be utilized to implement the various features and processes described herein.

FIG. 9 illustrates an exemplary computing device architecture that may be utilized to implement the various features and processes described herein. For example, the computing device architecture 900 could be implemented in wearable device 120, user device 150, or in any of the network servers of FIG. 1 or FIG. 2. Architecture 900 as illustrated in FIG. 9 includes memory interface 902, processors 904, and peripheral interface 906. Memory interface 902, processors 904 and peripherals interface 906 can be separate components or can be integrated as a part of one or more integrated circuits. The various components can be coupled by one or more communication buses or signal lines.

Processors 904 as illustrated in FIG. 9 is meant to be inclusive of data processors, image processors, central processing units, or any variety of multi-core processing devices. Any variety of sensors, external devices, and external subsystems can be coupled to peripherals interface 906 to facilitate any number of functionalities within the architecture 900 of the exemplar mobile device. For example, motion sensor 910, light sensor 912, and proximity sensor 914 can be coupled to peripherals interface 906 to facilitate orientation, lighting, and proximity functions of the mobile device. For example, light sensor 912 could be utilized to facilitate adjusting the brightness of touch surface 946. Motion sensor 910, which could be exemplified in the context of an accelerometer or gyroscope, could be utilized to detect movement and orientation of the mobile device. Display objects or media could then be presented according to a detected orientation (e.g., portrait or landscape).

Other sensors could be coupled to peripherals interface 906, such as a temperature sensor, a biometric sensor, or other sensing device to facilitate corresponding functionalities. Location processor 915 (e.g., a global positioning transceiver) can be coupled to peripherals interface 906 to allow for generation of geo-location data thereby facilitating geo-positioning. An electronic magnetometer 916 such as an integrated circuit could be connected to peripherals interface 906 to provide data related to the direction of true magnetic North whereby the mobile device could enjoy compass or directional functionality. Camera subsystem 920 and an optical sensor 922 such as a charged coupled device (CCD) or a complementary metal-oxide semiconductor (CMOS) optical sensor can facilitate camera functions such as recording photographs and video clips.

Communication functionality can be facilitated through one or more communication subsystems 924, which may include one or more wireless communication subsystems. Wireless communication subsystems 924 can include 802.x or Bluetooth transceivers as well as optical transceivers such as infrared. Wired communication subsystems can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 924 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.x communication networks, code division multiple access (CDMA) networks, or Bluetooth networks. Communication subsystem 924 may include hosting protocols such that the device may be configured as a base station for other wireless devices. Communication subsystems can also allow the device to synchronize with a host device using one or more protocols such as TCP/IP, HTTP, or UDP.

Audio subsystem 926 can be coupled to a speaker 928 and one or more microphones 930 to facilitate voice-enabled functions. These functions might include voice recognition, voice replication, or digital recording. Audio subsystem 926 in conjunction may also encompass traditional telephony functions.

I/O subsystem 940 may include touch controller 942 and/or other input controller(s) 944. Touch controller 942 can be coupled to a touch surface 946. Touch surface 946 and touch controller 942 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 946 may likewise be utilized. In one implementation, touch surface 946 can display virtual or soft buttons and a virtual keyboard, which can be used as an input/output device by the user.

Other input controllers 944 can be coupled to other input/control devices 948 such as one or more buttons, rocker switches, thumb-wheels, infrared ports, USB ports, and/or a pointer device such as a stylus. The one or more buttons (not shown) can include an up/down button for volume control of speaker 928 and/or microphone 930. In some implementations, device 900 can include the functionality of an audio and/or video playback or recording device and may include a pin connector for tethering to other devices.

Memory interface 902 can be coupled to memory 950. Memory 950 can include high-speed random access memory or non-volatile memory such as magnetic disk storage devices, optical storage devices, or flash memory. Memory 950 can store operating system 952, such as Darwin, RTXC, LINUX, UNIX, OS X, ANDROID, WINDOWS, or an embedded operating system such as VxWorks. Operating system 952 may include instructions for handling basic system services and for performing hardware dependent tasks. In some implementations, operating system 952 can include a kernel.

Memory 950 may also store communication instructions 954 to facilitate communicating with other mobile computing devices or servers. Communication instructions 954 can also be used to select an operational mode or communication medium for use by the device based on a geographic location, which could be obtained by the GPS/Navigation instructions 968. Memory 950 may include graphical user interface instructions 956 to facilitate graphic user interface processing such as the generation of an interface; sensor processing instructions 958 to facilitate sensor-related processing and functions; phone instructions 960 to facilitate phone-related processes and functions; electronic messaging instructions 962 to facilitate electronic-messaging related processes and functions; web browsing instructions 964 to facilitate web browsing-related processes and functions; media processing instructions 966 to facilitate media processing-related processes and functions; GPS/Navigation instructions 968 to facilitate GPS and navigation-related processes, camera instructions 970 to facilitate camera-related processes and functions; and instructions 972 for any other application that may be operating on or in conjunction with the mobile computing device. Memory 950 may also store other software instructions for facilitating other processes, features and applications, such as applications related to navigation, social networking, location-based services or map displays.

Each of the above identified instructions and applications can correspond to a set of instructions for performing one or more functions described above. These instructions need not be implemented as separate software programs, procedures, or modules. Memory 950 can include additional or fewer instructions. Furthermore, various functions of the mobile device may be implemented in hardware and/or in software, including in one or more signal processing and/or application specific integrated circuits.

Certain features may be implemented in a computer system that includes a back-end component, such as a data server, that includes a middleware component, such as an application server or an Internet server, or that includes a front-end component, such as a client computer having a graphical user interface or an Internet browser, or any combination of the foregoing. The components of the system can be connected by any form or medium of digital data communication such as a communication network. Some examples of communication networks include LAN, WAN and the computers and networks forming the Internet. The computer system can include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an API that can define on or more parameters that are passed between a calling application and other software code such as an operating system, library routine, function that provides a service, that provides data, or that performs an operation or a computation. The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer may employ to access functions supporting the API. In some implementations, an API call can report to an application the capabilities of a device running the application, such as input capability, output capability, processing capability, power capability, and communications capability.

FIGS. 10 A-D illustrates a series of examples as to how the health calculations of wearable devices may be improved.

FIG. 10A illustrates an exemplary wearable device that includes input from body sensor(s) 1000, an input over which communications from a geolocation data network 170 are received, and that outputs an adjusted health parameter 1020. The body sensor(s) 1000 may be one or more of the body sensors 130 of wearable device 120. The adjusted wearable data 1020 may be the output of one or both of the processes described in FIG. 4 or FIG. 5.

FIG. 10B illustrates an exemplary wearable device that includes input from body sensor(s) 1000, input from environment/weather sensor(s) 1010, and an output comprising improved weather data 1040.

FIG. 10C illustrates an exemplary wearable device that includes input from body sensor(s) 1000, input from geolocation data network 170, input from environment/weather sensor(s) 1010, and that outputs an adjusted health parameter 1020. The environment/weather sensor(s) 1010 may be one or more of the environment/weather sensor(s) 230 of wearable device 120. The adjusted wearable data 1020 may be the output of one or both of the processes described in FIG. 4 or FIG. 5, though further modified by the input from the environment/weather sensor(s) 1010, which may be treated similarly to the input from the geolocation data network 170 as another source of weather/environmental geolocation data. For example, when the wearable device is located in an area through which a low pressure system is moving, pressure sensor data measuring altitude may be adjusted to compensate for the presence of the low pressure system.

FIG. 10D illustrates an exemplary wearable device that includes all of the elements of FIG. 10C, but further includes a communication interface receiving information from a health network 270 and outputting recommendation 1030. In certain instances, the wearable device of FIG. 10D may display recommendations received from the health network 270 on a viewer 220 of the wearable device 120. An exemplary recommendation may advise a user of the wearable device to bring an umbrella or a rain coat to work because it is raining, or to take a break from running due to high heat and detected dehydration. In some embodiments, recommendation 1030 may project into the future—for example, by suggesting that a user take an umbrella or rain coat due to forecasted future rain, or to be careful when running because upcoming terrain is potentially dangerous (e.g., high elevations, rocky, slippery). Such future projections might also have an effect on sensor measurements (e.g., future rough terrain might stress the user out and cause a heightened pulse) and/or health parameter calculations (e.g., future rough terrain might make a user take extra precautions to successfully navigate it later, burning extra calories in the process). In certain embodiments, a user of the exemplary wearable device 120 of FIG. 10D may send a question to the health network 270 server. Such a question may relate to how to best protect user health from the weather over the next several hours or days. The user may then obtain a response from the health network 270 server through wearable device 120.

In some embodiments, the recommendations 1030 may take into account the user's historical data (e.g., from historical database 140 and 256). For example, if the user has been running for a number of weeks, the recommendation 1030 could suggest a break in order to decrease susceptibility to knee injury. Similarly, if the weather sensors 230 indicate that the user has been in a high-pollen environment often in the past week, the recommendation 1030 could suggest that the user stay indoors in order to avoid becoming sick.

Multiple methods of alerting the user about the recommendation may be used in addition to the viewer 220. These may include displaying a text notification, displaying a graphical notification, displaying a video notification, playing an audio notification, or initiating a vibration notification.

Figure 11A:
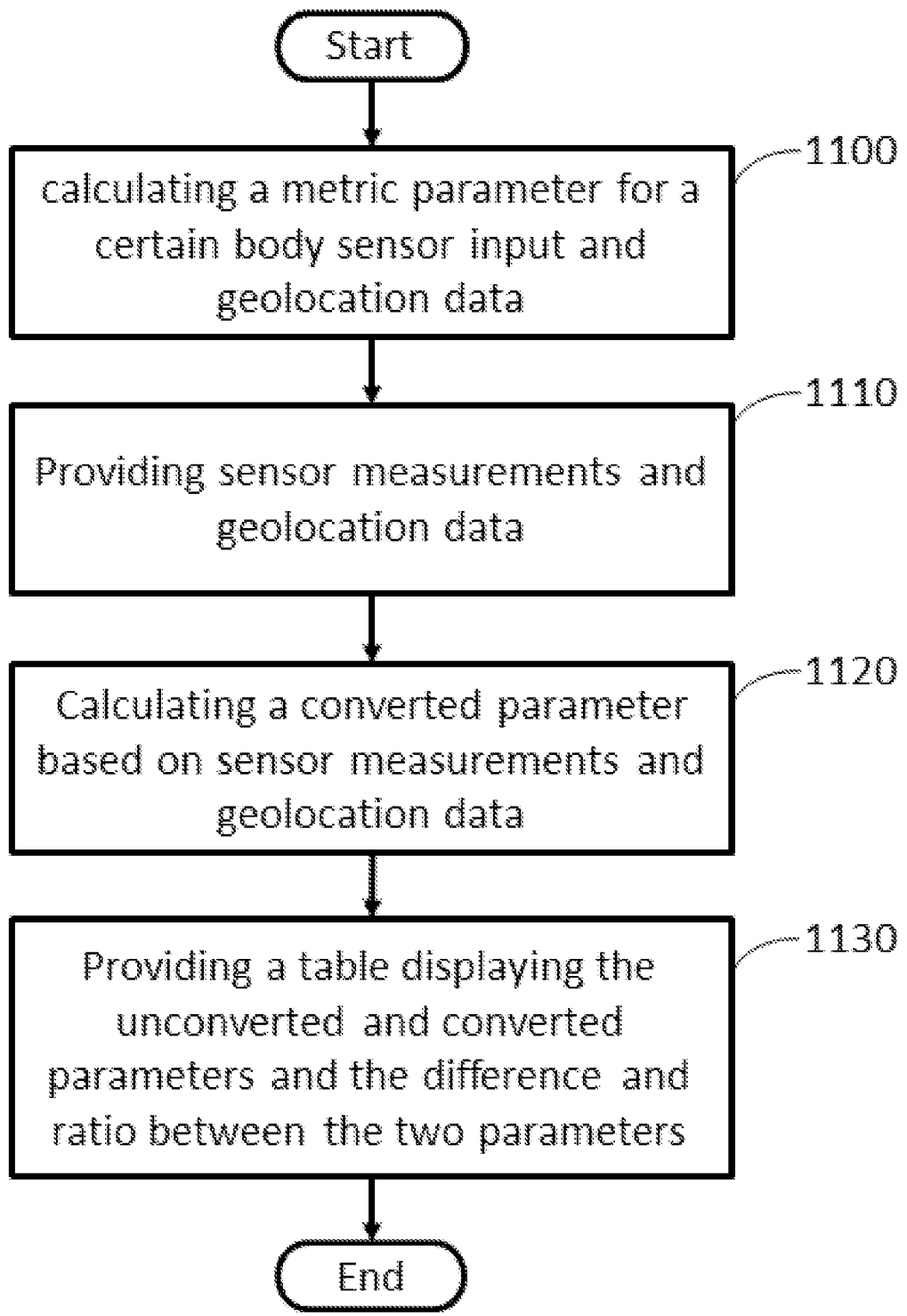
FIG. 11A illustrates an exemplary method for using network data.

FIG. 11A illustrates an exemplary method for using network data. Starting with step 1100, a health parameter (e.g., calories burned) for a given certain body sensor inputs and geolocation data (e.g., weather/environment/terrain data) is calculated using a number of database charts provided by the conversion database 144. For example, as seen in step 1100 of FIG. 11A, one example conversion database may include information pertaining to the amount of calories burned for a 1301*b* female on a walk/run with terrain having a certain percent incline. Other types of databases with various other data entries can be included here in order to provide a means to modify and provide a more accurate health parameter calculation (e.g., calories burned).

Next, sensor measurement history (e.g., from history database 140 of the wearable device 120 or synchronized history database 256 of the user device 150) and geolocation data (e.g., weather/environment/terrain data from data networks 160, 170, and 180) is provided (step 1110). Here, information regarding a user's run, for example, can be provided. As seen in step 1110 of FIG. 11, the direction, incline percent and length of different parts of the user's run are provided.

Calculations based on the sensor measurement and geolocation data is performed in the next step (step 1120). In particular, pulling from the conversion database, information can be obtained to associate segments of a user's run with the amount of calories burned. An exemplary embodiment of the conversion database 144 is shown in FIG. 11B.

Next, converted parameters 1134 (e.g., incorporating geolocation data) and unconverted parameters 1132 (e.g., not incorporating geolocation data) are provided (step 1130). In particular the converted parameters (generated above in step 1120) are used to compare the calculations that the wearable device 120 may provide based solely on its sensor data. A corresponding difference 1136 and ratio 1138 between the two parameters may also be calculated and stored in the wearable device 120 (e.g., at history database 140), at the user device 150 (e.g., at history database 256), or at the health network 270 (e.g., at health database 272).

Figure 11C:
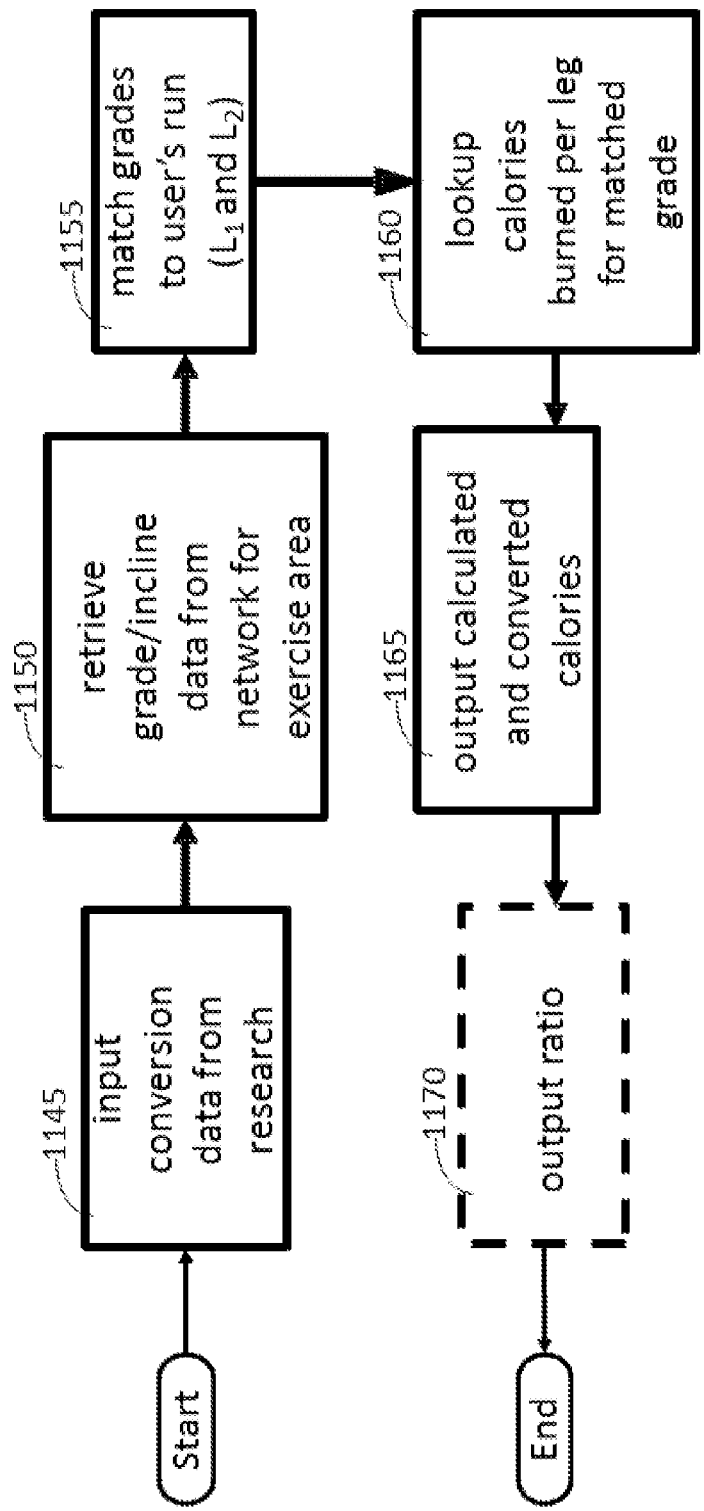
FIG. 11C is a flowchart illustrating an exemplary method for using network data in a conversion process

FIG. 11C is a flow diagram illustrating an exemplary process for using network data in a conversion process. This step includes obtaining conversion data (step 1145) (see step 1100 of FIG. 11A), retrieving the corresponding sensor measurements and geolocation data (e.g., grade/incline data) from the network for the exercise area (step 1150) (see step 1110 of FIG. 11A). Then the step matches the user's run with the geolocation information (e.g., grade/incline) (step 1155) (see steps 1110 and 1120 of FIG. 11A). The converted parameters 1132 and non-converted parameters 1134 are generated, compared (step 1160) (see step 1130 of FIG. 11A), and outputted (step 1165) (see step 1130 of FIG. 11A). A ratio 1138 between the converted parameters 1132 and non-converted parameters 1134 may then be calculated and outputted (step 1170) (see step 1130 column 1138 of FIG. 11A). This ratio 1138 may be used by operators or other systems to perform further conversions or to identify the magnitude of the error introduced by failing to adjust health related parameters to account for environmental measures.

Figure 12:
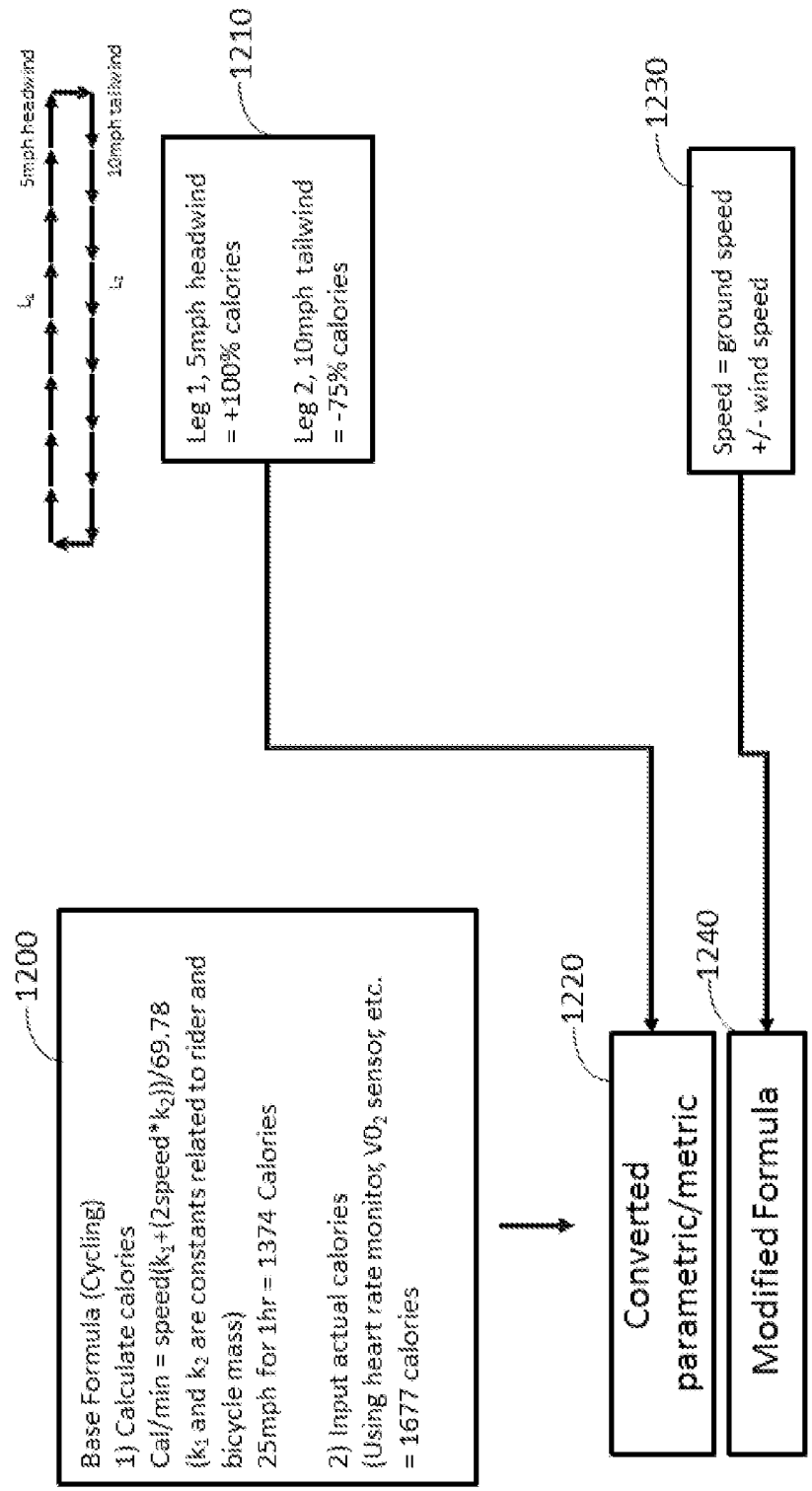
FIG. 12 is a block diagram illustrating an exemplary method for converted parameter.

FIG. 12 is a block diagram illustrating an exemplary method for calculating a converted parameter. As seen in FIG. 12, wind is being provided as geolocation data with respect to bicycling as the chosen exercise.

In particular, the method includes a base formula used to calculate the (non-converted) amount of calories burned (step 1200). Once that is ready, geolocation data (e.g., 5 mph headwind for a first leg of the bike path and 10 mph tailwind for a second leg of the bike path) may also be provided (step 1210). From this, a converted parameter can be calculated by applying the geolocation data's parameter adjustments (e.g., calorie adjustments) of step 1210 to the non-converted parameter calculated from the sensor measurements from step 1200 (step 1220).

As seen in FIG. 12, for part of the bike ride, the user was riding against the wind and therefore burned 100% more calories corresponding to the additional effort to bike against the wind. However, the user also bike with the wind resulting in 75% less calories burned. This provides a modifier to be used with respect to the base formula.

Figure 13:
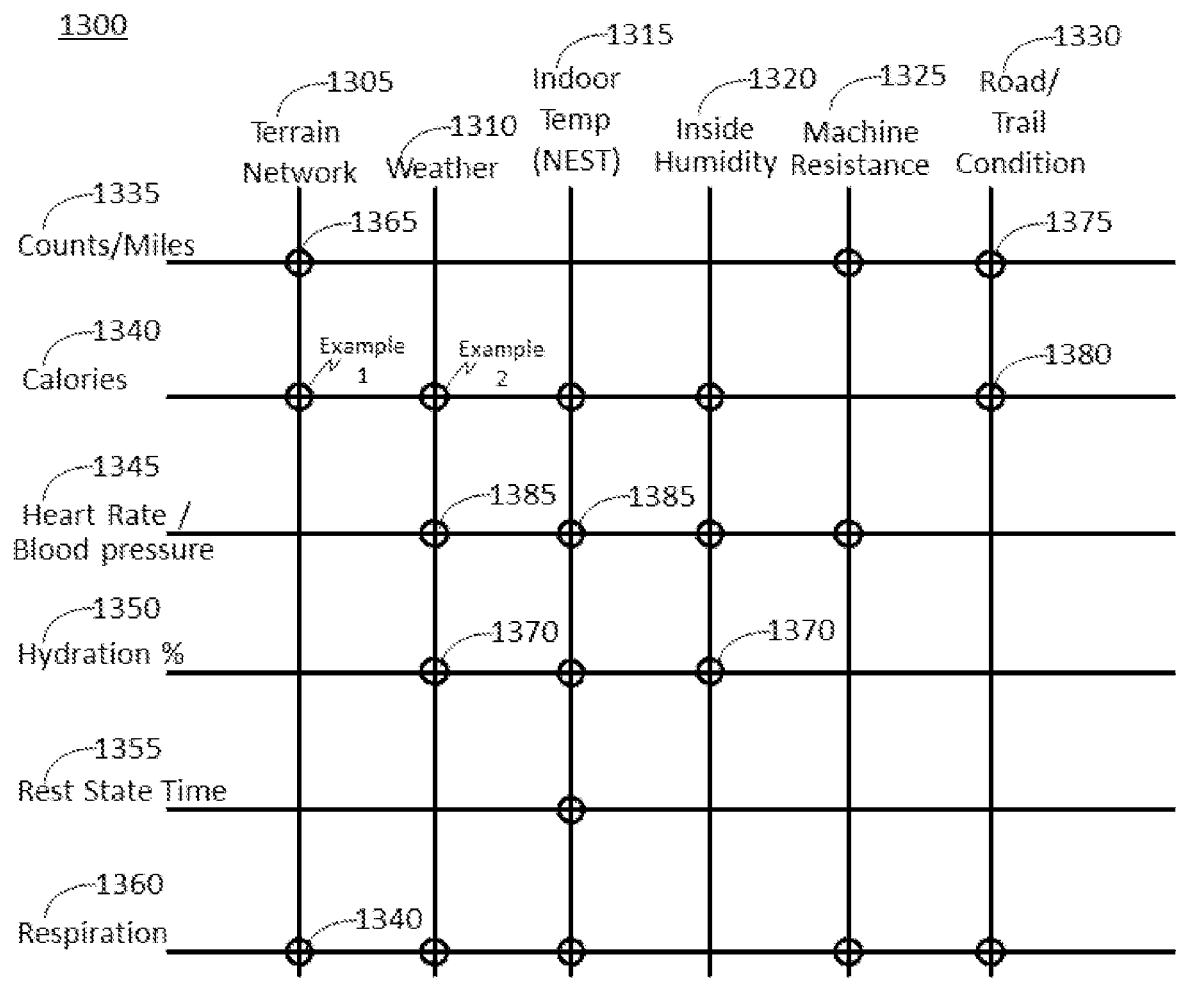
FIG. 13 illustrates an exemplary matrix showing combinations of various parameters and which location based data may affect calculation of that particular data.

An alternative method for calculating the amount of calories burned is also provided in FIG. 12 where the base formula can be modified into a modified formula 1240 to reflect geolocation data 1230, for example, that the speed of the user is the user's speed plus or minus the wind speed in the calculations (based on whether the user was biking with or against the wind). FIG. 13 illustrates an exemplary matrix 1300 showing combinations of various parameters and which location based data may affect calculation of that particular data. In a first example, calories can be affected by terrain as seen, for example, in FIG. 11A where percent incline can modify the amount of calories burned. In a second example, calories can also be affected by weather (e.g. wind) as shown in FIG. 12.

It should be noted that the table 1300 shown in FIG. 13 is not exhaustive of all possible crosses, parameters or location based data. More, less or different parameters, location based data or crosses can also be provided. The table 1300 shows possible interactions between geolocation data and health parameters. The geolocation data can include, for example, terrain network data 1305, weather data 1310, indoor temperatures 1315 (e.g., from a network-connected thermostat such as a Nest thermostat), indoor humidity 1320, gym machine resistance 1325, and road/trail condition 1330. The health parameters can include, for example, counts/distances 1335, calories 1340, heart rate/blood pressure 1345, hydration percentage 1350, rest state time 1355, and respiration 1360. These interactions may be explained in various ways. For example, the counts factor 1335 can be associated with inclines 1305 (shorter/longer steps) (intersection 1365). The hydration factor 1350 may be associated with outdoor humidity 1310 or indoor humidity 1320 (more humidity requires less hydration) (intersections 1370). A rough/broken trail 1330 may require shorter steps 1335 (intersection 1375). A rough/broken trail 1330 may also require more work and calories burned 1340 (intersection 1380). Cold outdoor temperatures 1310 and cold indoor temperatures 1315 may increase heart rate 1345 (to keep body warm) (intersection 1385). Hot outdoor temperatures 1310 and hot indoor temperatures 1315 may affect heart rate 1345 (to cool body) (also intersection 1385). Finally, elevation 1305 may affect oxygen level and thus respiration 1360 (intersection 1390).

Figure 14:
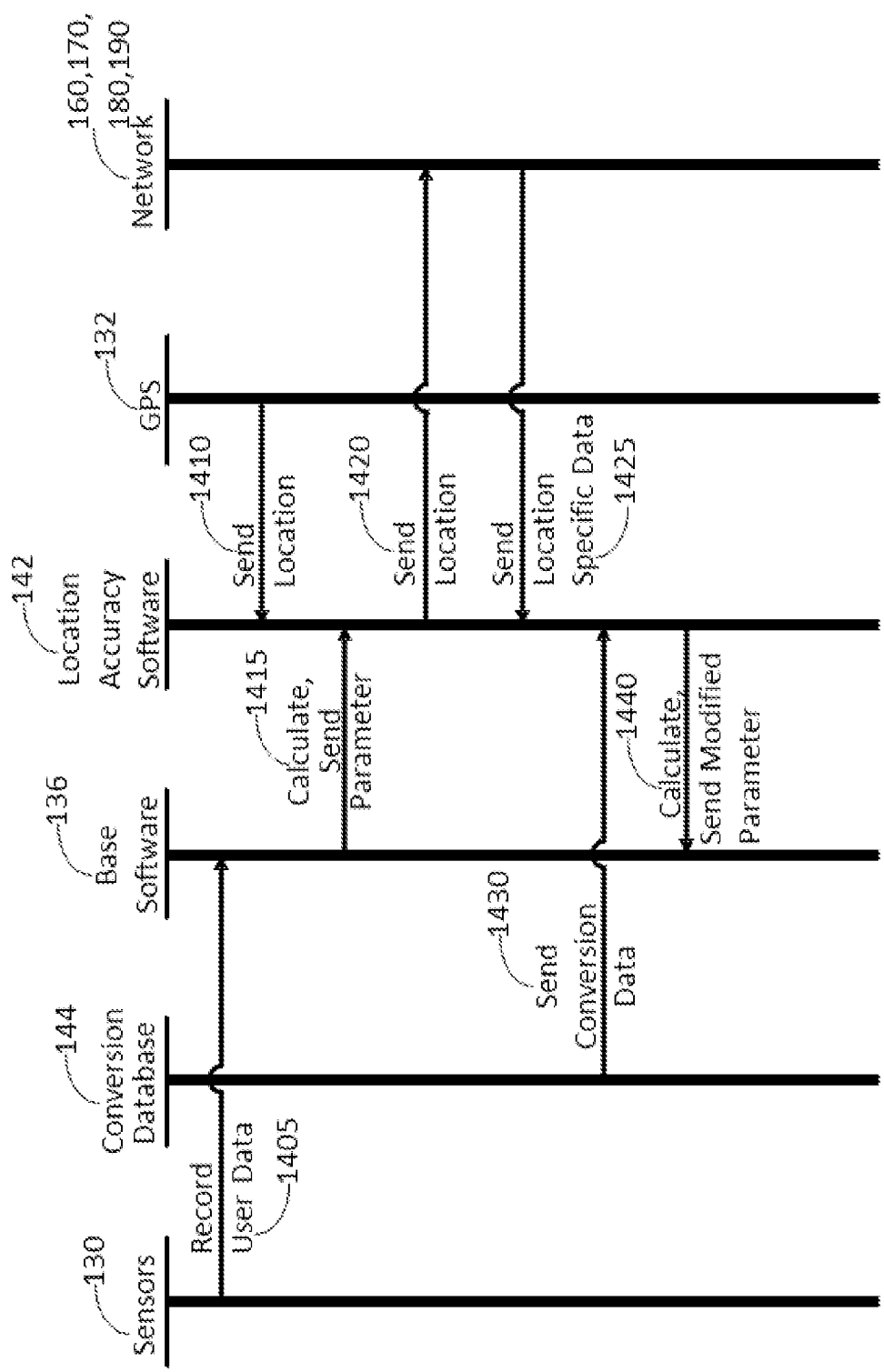
FIG. 14 illustrates an exemplary lane diagram showing the method for calculating a modified parameter as seen in FIG. 11A as disclosed herein.

FIG. 14 illustrates an exemplary lane diagram showing the method as disclosed herein. Here, the wearable device 120 first records user sensor measurement data (step 1405) from body sensors 130 (or from a history database 140) and transmits it to the base software 136 to calculate a non-converted health parameter (e.g. calories) during an exercise and send the non-converted health parameter value to the location accuracy software 142 of the wearable device 120 (step 1415). Meanwhile, the GPS module 132 of the wearable device 120 transmits the location of the wearable device 120 to the location accuracy software 142 of the wearable device 120 (step 1410). The wearable device then sends the GPS location data to external networks (e.g., data networks 160, 170, 180, and 190 from FIG. 1) (step 1420).

In response to the GPS data, the data networks 160, 170, 180, and 190 send location-based data (e.g., geolocation, weather, terrain, and environment data) to the location accuracy software 142 at the wearable device 120 (step 1425). Next, the conversion database 144 provides ratios in view of the location-based geolocation data to the location accuracy software 142 (step 1430) so that the software can calculate the modified or "converted" health parameter (e.g., calories) and transmit it back to the base software 136 (step 1440). From there, it may be stored, for example, in a history database 140 at the wearable device 120, a history database 256 at user device 150, or a health database at health network 270.

It should be noted that some steps, for example providing the GPS location to the location accuracy software 142, and the base software 136 calculating step for an initial output, can be performed in different order.

Figure 15:
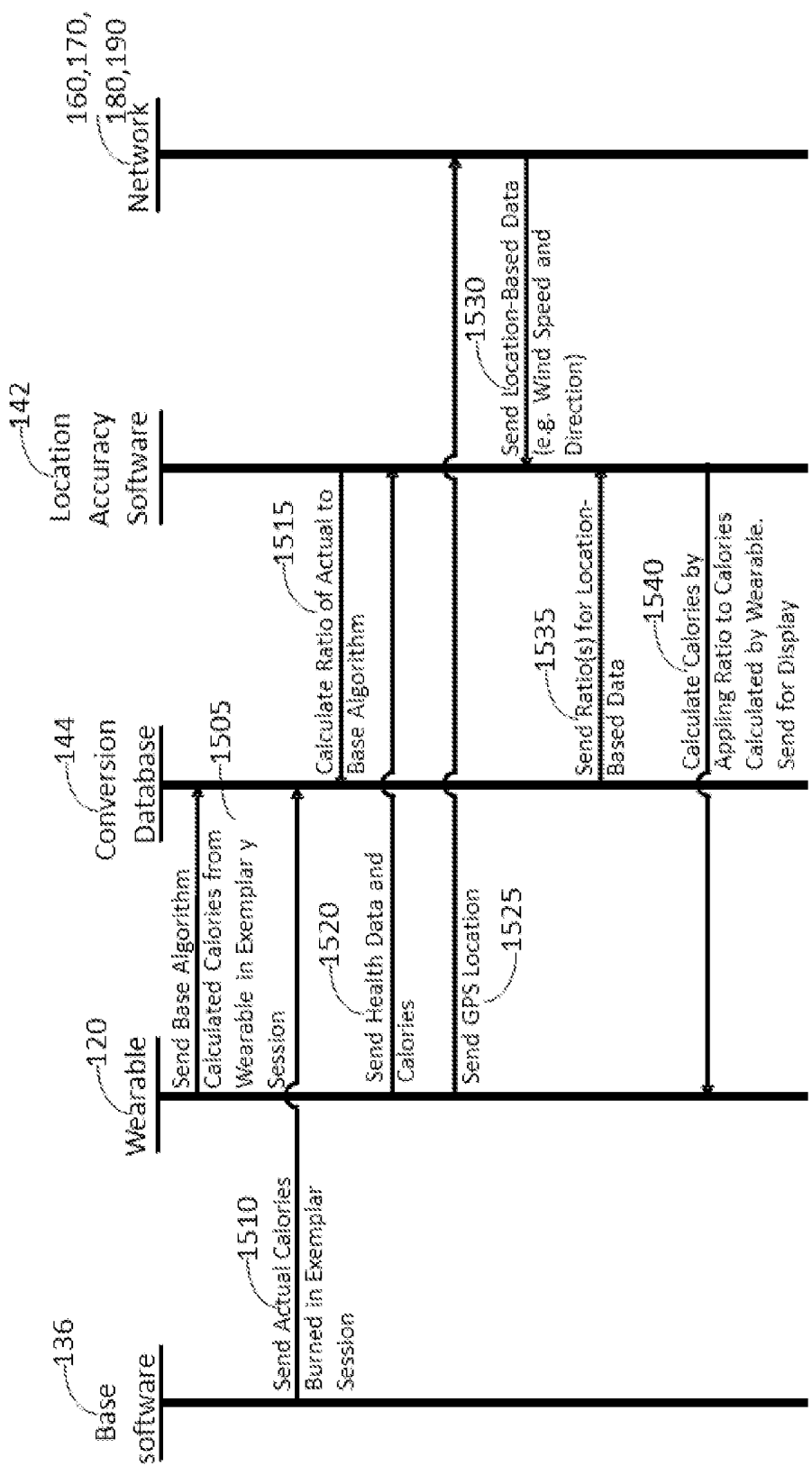
FIG. 15 illustrates an exemplary lane diagram showing the method for calculating a modified parameter as seen in FIG. 9 as disclosed herein.

FIG. 15 illustrates an exemplary lane diagram showing the method for calculating a modified parameter as seen in FIG. 12 as disclosed herein. Here, the wearable device 120 first sends the base algorithm used to calculate calories during an exercise trial to the conversion database 144 (step 1505). Next, the actual number of calories calculated by the base software 136 and based on body sensors 130 is sent to the conversion database 144 (step 1510). Next, the location accuracy software 142 calculates the ratio of actual to base calories from the base algorithm (step 1515). The wearable device 120 then sends health input data from a subsequent exercise session and calories calculated to the location accuracy software 142 (step 1520). The wearable device also sends related GPS data from GPS module 132 to data networks (e.g., data network 160, 170, 180, and 190 from FIG. 1) at this time (step 1525).

In response to the GPS data, the data networks 160, 170, 180, and 190 sends, to the wearable device 120, location-based data (e.g., geolocation, weather, terrain, environment data) which is provided to the location accuracy software 142 (step 1530). Next, the conversion database 144 provides ratios in view of the location based data to the location accuracy software 142 (step 1535) so that the location accuracy software 142 can calculate the modified or "converted" health parameter (e.g. calories) and send them to the wearable device 120 where they can be displayed (e.g., on a viewer 220) (step 1540).

FIG. 16 illustrates an exemplary history database 140 of the wearable device 120 and/or an exemplary history database 256 of user device 150. The history database 120 and 256 can include information that cross-references a date and/or time (column 1605) to a variety of other items. For example, the exemplary history database 120 and 256 can include body sensor measurements (e.g., blood pressure) of the body sensors 130 (column 1610), measurements from a weather temperature sensor of the weather sensors 230 (column 1615), a weather network temperature from a geolocation data network 170 (column 1620), adjusted blood pressure based on the weather measurements (column 1625), and a health summary (column 1630).

Dates in the table where the health thumbnail indicates that blood pressure ("BP") is OK (see blood pressure in column 1610 and column 1625, and health summary in column 1630) include 6-1-10, 6-2-10, 7-3-10, and 12-2-10. In certain entries, the blood pressure sensed (see blood pressure in column 1610) and the adjusted blood pressure (see adjusted blood pressure in column 1625) may be identical when the sensed temperature is between 71° F. and 73° F. (see sensed temperature in column 1615 or temperature provided by geolocation data network 170 in column 1620), and that the blood pressure sensed and the adjusted blood pressure may not be identical when the sensed temperature is around 19° F. This is because an algorithm may adjust the blood pressure reading measured when temperatures are cold.

A date where the blood pressure is indicated as being high (off average) is 12-2-11. The table indicates that on 12-2-11, a blood pressure sensed by the body sensor is 111, that the weather temperature sensed is 19° F., that the a temperature reported by the weather network is 20° F., that an adjusted blood pressure is 101, and that the health summary indicates that the user BP is high. Further, blood vessels near the surface of the skin may narrow in cold weather to conserve heat, thus increasing blood pressure.

Determinations relating to a user BP being OK or being high may be determined using data in a rule database 222. Temperature measurements listed in the table may vary from about 20° F. to about 70° F., a difference of about 50° F. When the temperature is 19° F., a rule in the rule database 222 indicates that blood pressure measured should adjusted by one count for every ten degrees of temperature reduction. Since on the date of 12-2-10, the measured blood pressure was 101 and the measured weather temperature was 19° F., since 70 minus 19 is approximately 50, the measured blood pressure should be adjusted downward by 5 counts. Since 101−5=96, and since a blood pressure reading of 96 is considered normal by the rule database 222, the health summary may therefore identify the BP as being OK.

It should be understood that the history databases 140 and 256 may also include other data. Most notably, the history databases 140 and 256 may store data about parameter calculations before and after modification (e.g., the outputs of FIG. 4 or FIG. 5) based on geolocation data (e.g., weather, environment, and terrain data).

Figure 17:
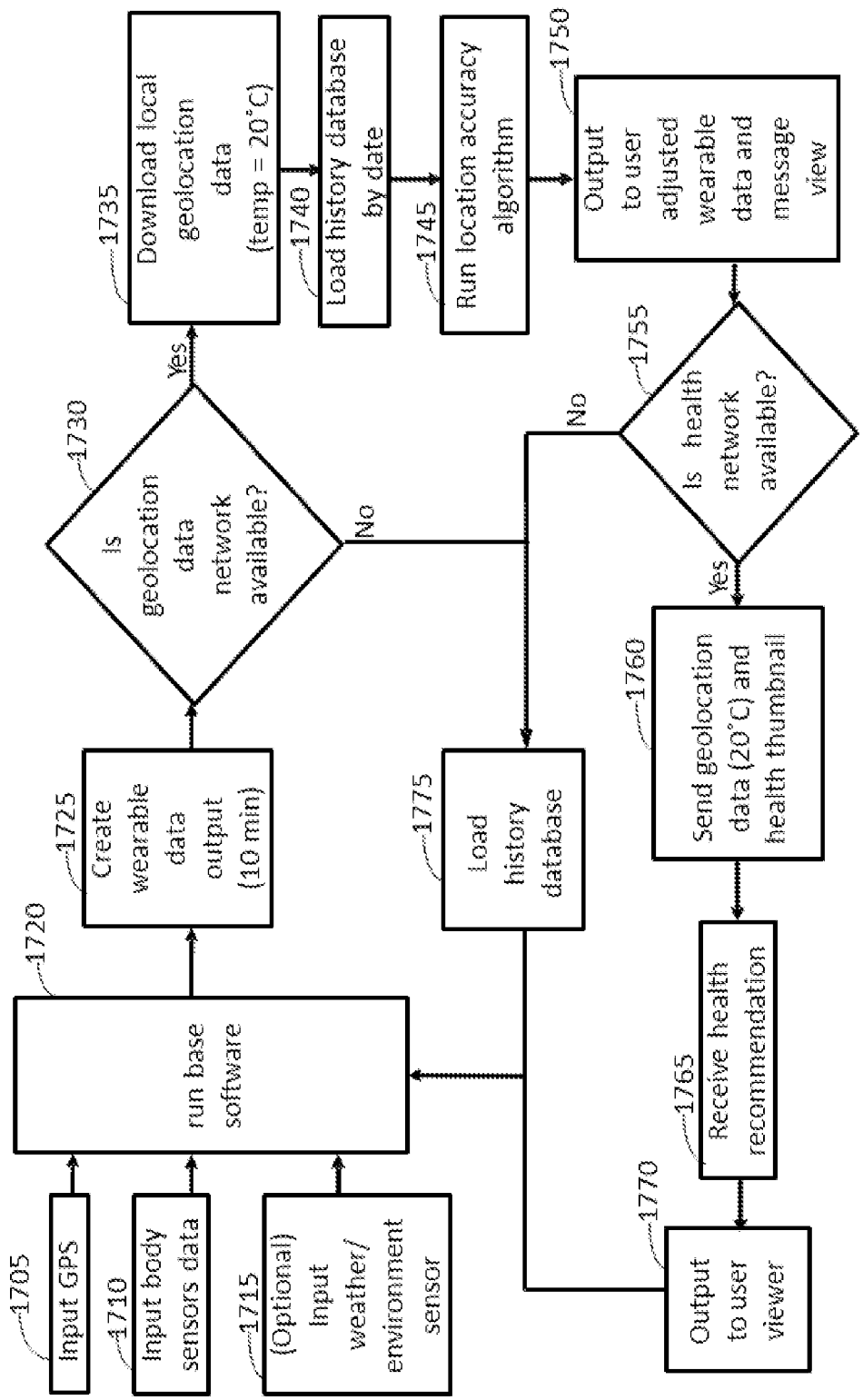
FIG. 17 is a flowchart of an exemplary method of location accuracy software sensor adjustment to a wearable device.

FIG. 17 is a flowchart of an exemplary method of location accuracy software 142 sensor adjustment to a wearable device 120. The method may be performed by a wearable device 120, a user device 150 tethered to a wearable device 120, or a user device 150 wirelessly communicating with a wearable device 120. In step 1705, GPS data from GPS module 132 may be inputted; in step 1710, body sensor data (e.g. from body sensors 130) may be inputted; and in step 1715, weather sensor data (e.g., from weather sensors 230) may be optionally inputted. In step 1720, the base software 136 may be run. In step 1725, a health parameter may be created by the wearable device 120 periodically (e.g., every 10 minutes). In step 1730, it may be determined whether a data network (e.g., data networks 160, 170, 180, and 190) is available. If so, the method proceeds to step 1735 where local geolocation data (e.g., indicating that the outdoor temperature is 20° C.) may be downloaded. In step 1740, a history database 140 and 256 may load historic data by date. In step 1745, a location accuracy software 142 may be executed by a processor to modify the health parameter (e.g., modified blood pressure based on weather) or to modify a calculated health parameter (e.g., modified calories burned number), and in step 1750, a result of the execution may be outputted as a message on a display.

In step 1755, it may be determined whether a health network 270 is available. If so, the method proceeds to step 1760 where geolocation data (e.g., temperature of 20° C.) may be sent to the health network 270 server, and in step 1765, a health recommendation 1030 may be received by the wearable device 120 from the health network 270 server. Then in step 1770, the health recommendation 1030 may be presented to a user of the wearable device 120 for the user to view on a viewer 220. After step 1770, the method may return to step 1720.

When it may be determined in step 1730 that data networks 160, 170, 180, and 190 are not available, or in step 1755 that the health network 270 is not available, the method may proceed directly to step 1775 where historic data is loaded from the history database 140 and 256. FIG. 17 also references the rule for adjusting blood pressure as discussed above in the description of FIG. 16.

Figure 18A:
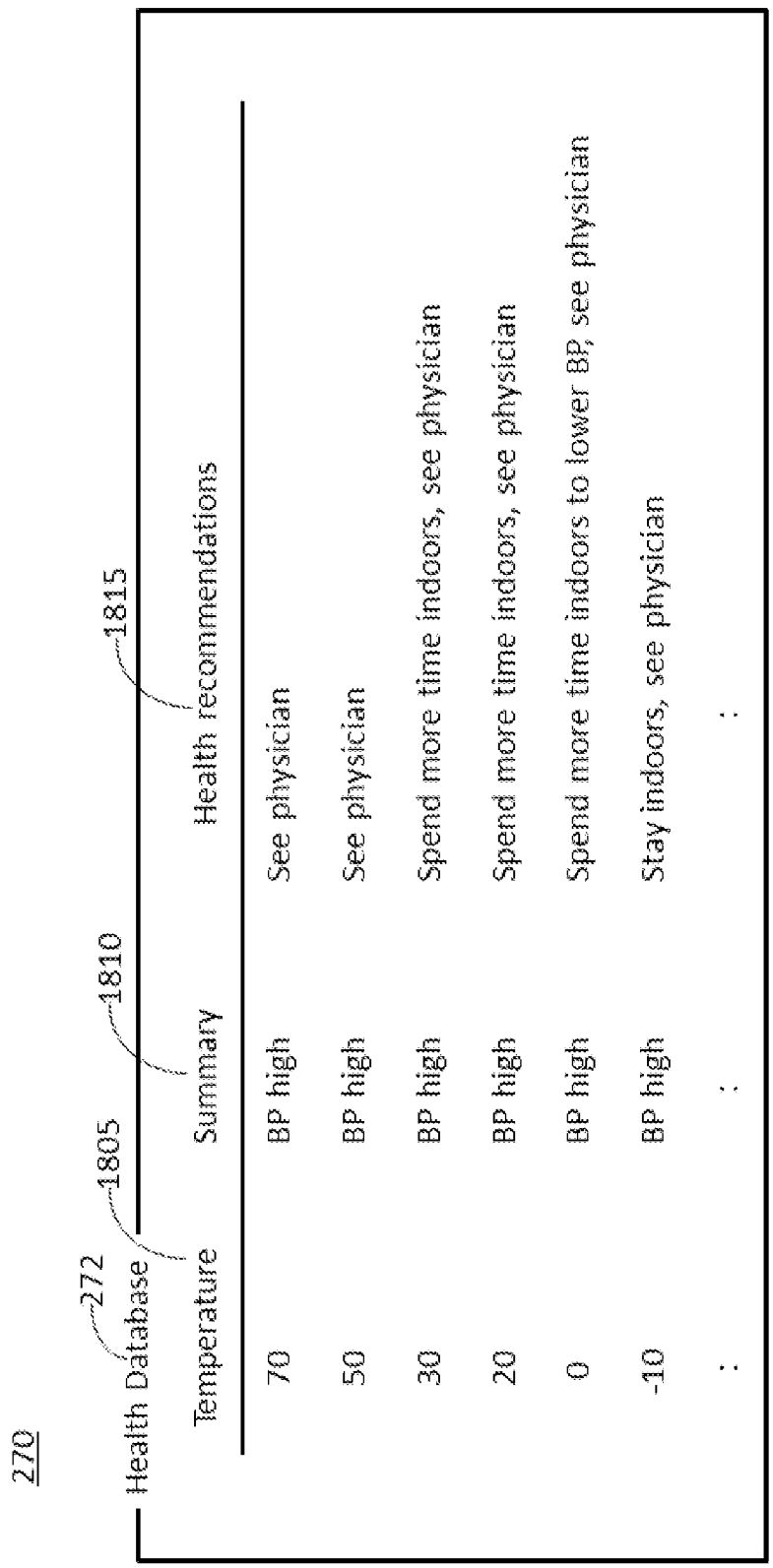
FIG. 18A illustrates an exemplary health database of the health network.

FIG. 18A illustrates an exemplary health database 272 of the health network 270. The information from the health database 272 may include temperatures (column 1805) ranging from 70° F. down to minus 10° F., health summaries (column 1810) indicating that a user BP is high, and various recommendations (1815) from the health network 270. The recommendations in FIG. 18A may include notifications to see physician, spend more time indoors, see physician, spend more time indoors to lower BP, and stay indoors, see physician, or other recommended actions. In some embodiments, the recommendations may come from a third party 280 through the API 276 of the health network 270, so that doctors 282, online medical resources 284 (e.g., WebMD), users 286, and other individuals or groups 288 can assist in providing recommendations. In particular, the other groups 288 may include caregivers, so that an elderly or disabled patient might receive customized recommendations to take certain medications or based on their activities. In particular, the other groups 288 might also include advertisers, who could provide the wearable device with recommendations to remedy an issue that the user is facing (e.g., as measured by body sensors 130 or weather sensors 230 or geolocation data from data networks 160, 170, 180, and 190), such as hydrating drinks, blood pressure medications, stress medications, blood sugar sources (e.g., food), insulin sources, asthma inhalers, better exercise gear (e.g., running shoes, weights, ankle/knee/arm braces), or other medications, clothing, consumables, or objects that might be helpful to the user. In an embodiment of the invention, the health database 272 is in form of a table.

Figure 18B:
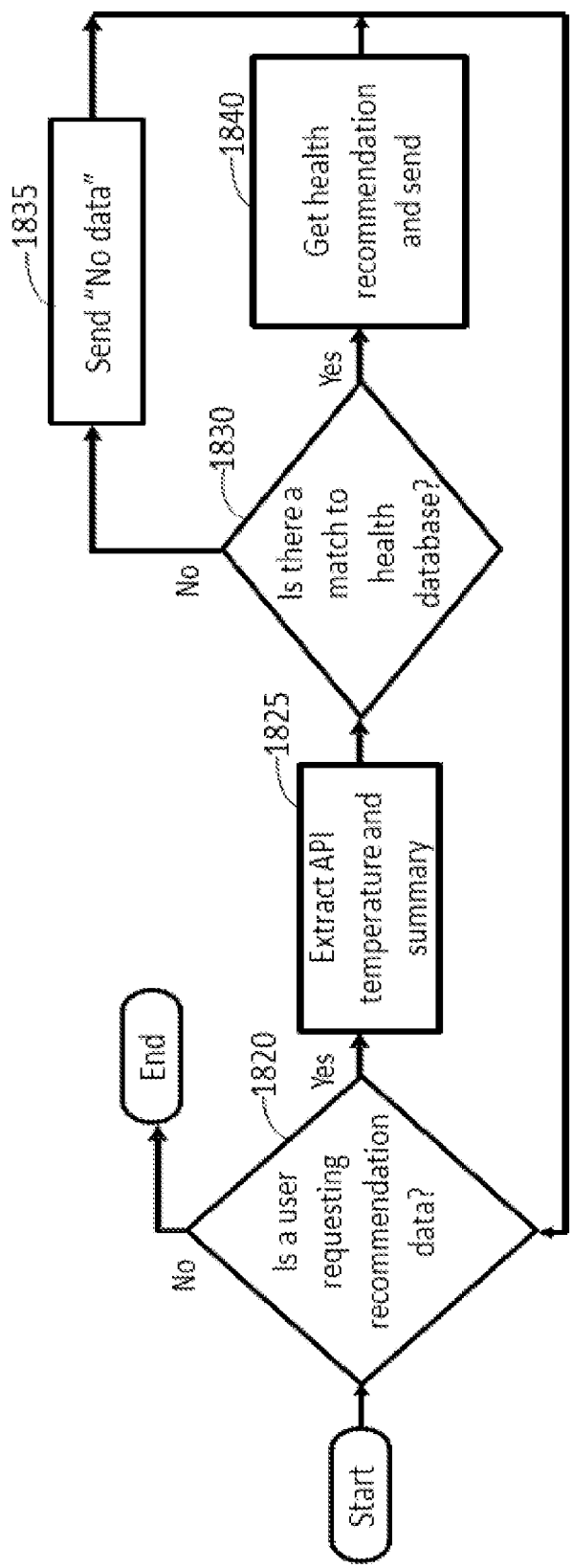
FIG. 18B is a flowchart illustrating exemplary operations for an exemplary sensor measurement adjustment at the location accuracy software of a wearable device.

FIG. 18B is a flowchart illustrating exemplary operations for an exemplary sensor measurement adjustment at the location accuracy software 142 of a wearable device 120. During these exemplary operations, it may be determined whether a user is requesting recommendation data in step 1820. If so, an API 276 may extract a temperature (column 1805 of FIG. 18A) and a health summary (column 1810 of FIG. 18A) in step 1830. Then, it may be determined whether the temperature and the summary match an entry in the health database 272 in step 1835. If so, a health recommendation 1030 may be retrieved and sent in step 1840, and the process can be restarted. If it is determined that there is no match in the health database 272, no data may be sent in step 1840. Then, the method may return to determine whether the user is requesting recommendation data in step 1820. If not, the method may end in step 1825.

Figure 19:
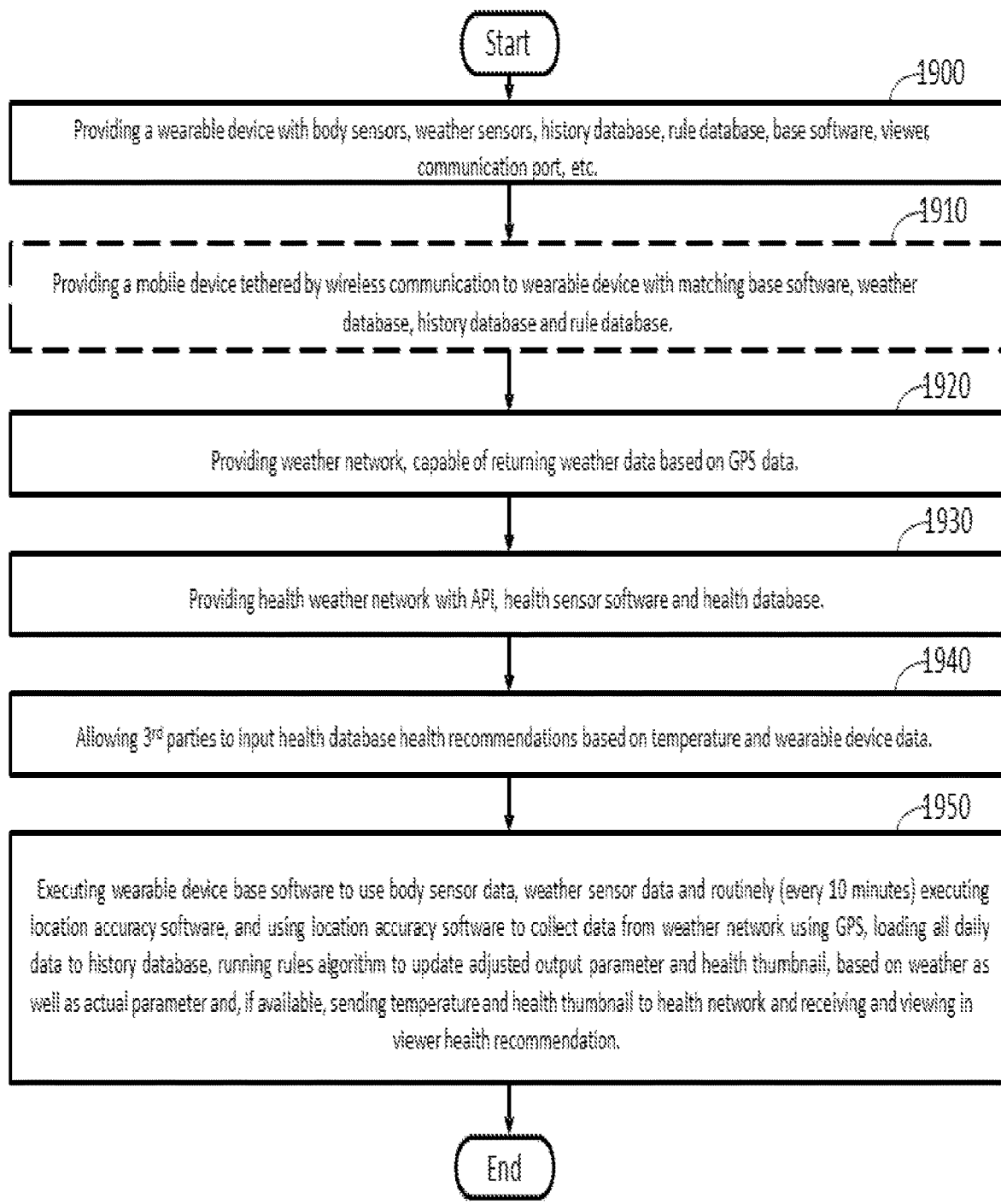
FIG. 19 illustrates an exemplary method of sensor measurement adjustment at the location accuracy software of a wearable device.

FIG. 19 illustrates an exemplary method of sensor measurement adjustment at the location accuracy software 142 of a wearable device 120. In step 1900, a wearable device 120 may be provided with body sensors 130, weather sensors 230, history database 140, rule database 222, base software 136, a viewer 220, and a communication port 126.

A user device 150 may be tethered to the wearable device 120 by a wireless communication interface 152. In step 1910, the user device 150 may optionally be provided with matching base software 250, a geolocation data database 254, a history database 256, and a rule database.

One or more data networks 160, 170, 180, and 190 may then provide environment/weather/terrain data corresponding to a GPS location of the wearable device 120 in step 1920.

Next, a health network 270 may be provided with an API 276, health software 274, and a health database 272 in step 1930. Third parties 280 may be allowed to input health recommendations 1030 into the health database 272. The recommendations 1030 may correspond to temperatures measured at the data networks 160, 170, 180, and 190 and/or by the wearable device 120 in step 1940. In some embodiments, the health network 270 may detect the type of the wearable device 120 (e.g., what body sensors 130 and/or weather sensors 230 is contains) and customize its operations proactively based on this type, or transmit customized software to the wearable device 120 based on this type, or, later, transmit customized recommendations 1030 based on this type.

Base software 136 executing on a processor 122 at the wearable device 120 may body sensor data 130, weather sensor data 230 to routinely (e.g., every 10 minutes) to execute location accuracy software 142. Location accuracy software 142 may be used to collect data from the data networks 160, 170, 180, and 190 using the GPS data from the GPS module 132 of the wearable device 120, load data collected to a history database 140 and 256 daily, and run a rules/conversion algorithm that adjusts parameters and health summaries. The adjustments to the health summaries and the health parameters may be based on weather, environment, terrain, and other geolocation data. Actual measurements such as measured blood pressure or temperature and calculated health parameters such as calorie counts and health summaries may be sent to the health network 270. Furthermore, recommendations 1030 received from the health network 270 may be displayed on a viewer 220 for the user of the wearable device 120 to view in this step in step 1950.

Although each exemplary operations illustrated by FIGS. 1-19 and accompanying text recites steps performed in a particular order, the present invention does not necessarily need to operate in that recited order. One of ordinary skill in the art would recognize many variations, including performing steps in a different order.

The software components described above, such as base software 136, location accuracy software 142, base wearable device software 250, heath software 274, weather software 228, etc. may be stored in the memory of the corresponding device, such as wearable device 120 executing the software or the memory of another network-connected device, such as user device 150. The processing unit of the device executing the software interacts with the stored softwares in the memory to execute the softwares. In some embodiments, the software components may be stored in the memory of the processing unit itself.

Various examples of the network 100 include but are not limited to the Internet, intranets, extranets, wired networks, wireless networks, wide area networks (WANs), local area networks (LANs), or other suitable networks, etc., or any combination of two or more such networks.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claim.

The invention claimed is:

1. A computer implemented method for health calculations, the method comprising:

receiving health input data captured using a plurality of sensors of a wearable device worn by a user while the user is performing two or more activities, the health input data comprising movement data capturing movement of the user while the user is performing the two or more activities and location data capturing one or more locations of the user while the user is performing the two or more activities, wherein the two or more activities comprise a first activity followed by at least a second activity, and wherein the movement data is captured using an accelerometer of the wearable device;

obtaining location-based information associated with the location data capturing the one or more locations of the user while the user is performing the two or more activities;

segmenting the movement data into two or more segments based on characteristics of the movement data including an amplitude and a frequency of one or more portions of the movement data;

categorizing each of the two or more segments of the movement data as matching one of the two or more activities of the user based on the characteristics of the movement data including the amplitude and the frequency of the one or more portions of the movement data;

refining the categorization of the segmented movement data based on the location-based information;

calculating a heath parameter based on the location-based information, the health input data, and the refined categorization of the movement data; and rendering output based on the health parameter via the wearable device to the user;

wherein the location-based information comprises at least one of: outdoor humidity, outdoor temperature, outdoor ultraviolet radiation, outdoor pollen density, outdoor wind direction, outdoor wind velocity, outdoor terrain roughness, outdoor road condition, outdoor trail condition, current season, indoor temperature, indoor humidity, gym equipment resistance, gym equipment difficulty level, and environmental stress level.

2. The method of claim 1, further comprising at least one of:

transmitting the location data capturing the one or more locations of the user while the user is performing the two or more activities to a network server and receiving the location-based information associated with the location data from the network server.

3. The method of claim 2, wherein the location-based information corresponding to the location data capturing the one or more locations of the user while the user is performing the two or more activities is an average of a plurality of location-based information data points stored at the network server corresponding to a predetermined radius of the one or more locations of the user.

4. The method of claim 1, further comprising:
receiving environmental data captured using one or more of the plurality of sensors of the wearable device worn by the user while the user is performing the two or more activities, the environmental data including one or more ambient environmental values; and
modifying the calculated health parameter based on the one or more environmental values.

5. The method of claim 1, wherein rendering output based on the health parameter via the wearable device to the use comprises: rendering an alert to notify the user of the wearable device about a recommendation, wherein the alert comprises at least one of: displaying a text notification, displaying a graphical notification, displaying a video notification, playing an audio notification, and initiating a vibration notification.

6. The method of claim 1 further comprising generating an alert based on the health parameter.

7. The method of claim 1, wherein calculating the health parameter comprises modifying the calculated health parameter using rules that are specific to the type of health parameter.

8. The method of claim 1, wherein the plurality of sensors of the wearable device work by the user measure at least one of a blood oxygen level, a hydration level, a blood pressure, a blood sugar level, a blood glucose level, an insulin level, a body temperature, a heart rate, a weight, a sleep quality, a number of steps, a velocity of movement, an acceleration of movement, a vitamin level, a respiratory rate, a heart sound, a breathing sound, a skin moisture, a sweat level, a sweat composition, and a nerve firing.

9. The method of claim 1, wherein the categorization is refined based on one or more of: GPS data, terrain data, and temperature data.

10. The method of claim 1, wherein calculating the health parameter based on the location-based information, the health input data, and the refined categorization of the movement data comprises disregarding certain segments of the movement data from a determination of the health parameter.

11. The method of claim 1, further comprising:
further refining the categorization of the segmented movement data from walking to swimming when the location-based information indicates that a user is in a body of water; and/or
further refining the categorization of the segmented movement data from walking to driving when the location-based information indicates that a user is located on a highway; and/or
further refining the categorization of the segmented movement data as sailing or boating when the location-based information indicates that a user is in a body of water, and the movement data indicates that the user is moving in a consistent direction; and/or
further refining the categorization of the segmented movement data as running when the location-based information indicates that a user is in a body of water, and the movement data indicates that the user is moving in a varying direction; and/or
further refining the categorization of the segmented movement data as exercising when the location-based information indicates that a user is in a gymnasium, GPS data indicates that the user is stationary, and the movement data indicates that a user is moving.

* * * * *